United States Patent
Roundy et al.

(10) Patent No.: US 11,051,814 B2
(45) Date of Patent: Jul. 6, 2021

(54) BIOABSORBABLE CLIPS AND APPLICATOR FOR TISSUE CLOSURE

(71) Applicant: OREGON HEALTH & SCIENCE UNIVERSITY, Portland, OR (US)

(72) Inventors: Neil Roundy, Portland, OR (US); Rachel Dreilinger, Lake Oswego, OR (US)

(73) Assignee: Oregon Health & Science University, Portland, OR (US)

(*) Notice: Subject to any disclaimer, the term of this patent is extended or adjusted under 35 U.S.C. 154(b) by 155 days.

(21) Appl. No.: 14/486,649

(22) Filed: Sep. 15, 2014

(65) Prior Publication Data

US 2015/0080914 A1 Mar. 19, 2015

Related U.S. Application Data

(60) Provisional application No. 61/878,298, filed on Sep. 16, 2013.

(51) Int. Cl.
*A61B 17/08* (2006.01)
*A61B 17/128* (2006.01)
(Continued)

(52) U.S. Cl.
CPC .......... *A61B 17/083* (2013.01); *A61B 17/128* (2013.01); *A61B 17/1227* (2013.01);
(Continued)

(58) Field of Classification Search
CPC ........ A61B 17/0487; A61B 2017/0488; A61B 17/08; A61B 17/128; A61B 17/064;
(Continued)

(56) References Cited

U.S. PATENT DOCUMENTS 3,378,010 A * 4/1968 Codling ............... A61B 17/122
606/142
3,601,127 A 8/1971 Finegold
(Continued)

FOREIGN PATENT DOCUMENTS

CN 103989501 8/2014
EP 0469524 2/1992
(Continued)

OTHER PUBLICATIONS

CN103989501, Google Translation of CN103989501, as early as Jun. 17, 2018, 11 pages.
(Continued)

*Primary Examiner* — Tan-Uyen T Ho
*Assistant Examiner* — Charles M Wei
(74) *Attorney, Agent, or Firm* — Schwabe, Williamson & Wyatt, P.C.

(57) ABSTRACT

Surgical clips and surgical applicators used in performing rapid tissue closure in either minimally invasive surgeries or traditional open procedures are provided. In one example approach, a surgical clip comprises opposing sides extending from a top portion and terminating at tips positioned below the top portion. The resting position of the clip is its closed position, and in the closed position, the tips are set at a first distance apart. Each side has a cut-out (or hole or aperture) opposite one another. Each cut-out is fully surrounded by the side and does not extend to the top or tips. Each cut-out is configured to engage an inwardly turned hook at the end of a clip array or clip applicator such that the sides bend outwardly away from each other when pressure is applied on the top portion of the clip, thereby placing the clip in an open position.

34 Claims, 24 Drawing Sheets

(51) Int. Cl.
*A61B 17/122* (2006.01)
*A61B 17/064* (2006.01)
*A61B 17/068* (2006.01)
*A61B 17/00* (2006.01)
*A61B 17/02* (2006.01)
*A61B 17/34* (2006.01)

(52) U.S. Cl.
CPC ...... *A61B 17/1285* (2013.01); *A61B 17/0293* (2013.01); *A61B 17/0682* (2013.01); *A61B 17/3421* (2013.01); *A61B 2017/00902* (2013.01); *A61B 2017/0641* (2013.01); *A61B 2017/0645* (2013.01)

(58) Field of Classification Search
CPC ........ A61B 2017/0641; A61B 17/0642; A61B 2017/0645; A61B 17/0644; A61B 17/0643; A61B 17/068; A61B 2017/0646; A61B 2017/0688; A61B 17/07207; A61B 2017/072; A61B 2017/081; A61B 17/083; A61B 17/122; A61B 17/1222; A61B 2017/1225; A61B 17/1227; A61B 17/1285; A61B 2017/00004; A61B 17/10; A61B 17/285
USPC .................... 606/151, 157, 158, 219, 143
See application file for complete search history.

(56) References Cited

U.S. PATENT DOCUMENTS

| | | | |
|---|---|---|---|
| 4,217,902 A * | 8/1980 | March ................. | A61B 17/083 606/157 |
| 4,821,721 A | 4/1989 | Chin et al. | |
| 4,983,176 A * | 1/1991 | Cushman ............. | A61B 17/083 606/142 |
| 5,007,921 A | 4/1991 | Brown | |
| 5,192,288 A | 3/1993 | Thompson et al. | |
| 5,207,692 A * | 5/1993 | Kraus ................. | A61B 17/083 227/901 |
| 5,425,489 A | 6/1995 | Shichman et al. | |
| 5,591,178 A | 1/1997 | Green et al. | |
| 5,725,542 A * | 3/1998 | Yoon ................. | A61B 17/0487 606/139 |
| 5,779,720 A | 7/1998 | Walder-Utz et al. | |
| 6,120,526 A | 9/2000 | Daley | |
| 6,283,984 B1 | 9/2001 | Ray | |
| 6,352,541 B1 * | 3/2002 | Kienzle ............. | A61B 17/1285 606/143 |
| 6,425,903 B1 | 7/2002 | Voegele | |
| 6,537,289 B1 * | 3/2003 | Kayan ................. | A61B 17/122 606/157 |
| 6,679,894 B2 * | 1/2004 | Damarati ............. | A61B 17/122 29/243.56 |
| 7,533,790 B1 | 5/2009 | Knodel et al. | |
| 8,075,481 B2 * | 12/2011 | Park ................. | A61B 17/0218 600/204 |
| 8,393,517 B2 | 3/2013 | Milo | |
| 9,358,008 B2 * | 6/2016 | Mazzucco ............ | A61B 17/083 |
| 9,883,866 B2 | 2/2018 | Roundy et al. | |
| 2002/0111641 A1 | 8/2002 | Peterson et al. | |
| 2004/0059378 A1 | 3/2004 | Peterson et al. | |
| 2004/0087985 A1 * | 5/2004 | Loshakove ........ | A61B 17/0057 606/153 |
| 2004/0138705 A1 * | 7/2004 | Heino ................. | A61B 17/064 606/219 |
| 2004/0138765 A1 * | 7/2004 | Bonissone ........... | B28C 7/0404 700/31 |
| 2005/0107807 A1 * | 5/2005 | Nakao ................ | A61B 17/1222 606/139 |
| 2005/0149064 A1 | 7/2005 | Peterson et al. | |
| 2005/0216036 A1 * | 9/2005 | Nakao ................. | A61B 17/068 606/142 |
| 2007/0208358 A1 | 9/2007 | Kayan | |
| 2008/0065154 A1 | 3/2008 | Allard et al. | |
| 2008/0103510 A1 * | 5/2008 | Taylor ................... | A61B 17/08 606/143 |
| 2008/0312670 A1 | 12/2008 | Lutze et al. | |
| 2009/0072006 A1 | 3/2009 | Clauson et al. | |
| 2009/0206144 A1 * | 8/2009 | Doll ................. | A61B 17/07207 227/177.1 |
| 2010/0010511 A1 | 1/2010 | Harris et al. | |
| 2010/0016875 A1 * | 1/2010 | Nakao ................. | A61B 17/221 606/159 |
| 2010/0191262 A1 | 7/2010 | Harris et al. | |
| 2010/0191282 A1 | 7/2010 | Harris et al. | |
| 2010/0204717 A1 | 8/2010 | Knodel | |
| 2010/0312259 A1 | 12/2010 | Houser et al. | |
| 2011/0112551 A1 * | 5/2011 | Adams ................ | A61B 17/122 606/142 |
| 2013/0172914 A1 * | 7/2013 | Weisshaupt ........ | A61B 17/1227 606/151 |
| 2014/0128819 A1 | 5/2014 | Eaves | |
| 2015/0080914 A1 | 3/2015 | Roundy et al. | |

FOREIGN PATENT DOCUMENTS

| | | | |
|---|---|---|---|
| EP | 0565892 | 10/1993 | |
| EP | 0565892 A1 | 10/1993 | |
| JP | A-S58-138447 | 8/1983 | |
| JP | A_H05-007593 | 1/1993 | |
| JP | 3124027 | 10/2000 | |
| JP | 3124027 | 1/2001 | |
| JP | 3124027 B2 * | 1/2001 | ........... A61B 17/083 |
| JP | 2005/530559 | 10/2005 | |
| JP | 2005530559 | 10/2005 | |
| JP | 2017/523810 | 8/2017 | |
| WO | WO 1990/010418 | 9/1990 | |
| WO | 2011059666 A2 | 5/2011 | |
| WO | WO 2011/059666 | 5/2011 | |
| WO | 2012/135735 A2 | 10/2012 | |
| WO | WO 2012/135735 | 10/2012 | |
| WO | WO 2016/073376 | 5/2016 | |

OTHER PUBLICATIONS

JPS58138447, Machine Translation of JPS58138447, J-Plat Pat, as early as Jul. 10, 2018, 5 pages.
Braun et al., Surgical Staple, U.S. Pat. No. 4,505,273, Mar. 19, 1985, found in Espacenet as an "Also Published As" document for Japanese Document JPS58138447, used here as the English translation thereof, 6 pages, United States.
Kraus et al., Surgical Clip Applier with Reciprocating Clip Sleeve and Dual Ratchet Mechanism,. U.S. Pat. No. 5,207,692, May 4, 1993, found in Espacenet as an "Also Published As" document for Japanese Document JPA_H05-007593, used here as the English translation thereof, 23 pages, United States.
Patent Cooperation Treaty; International Preliminary Report on Patentability; International Search Report and Written Opinion of PCT/US2015/058669; dated May 9, 2017; 6 pages.

\* cited by examiner

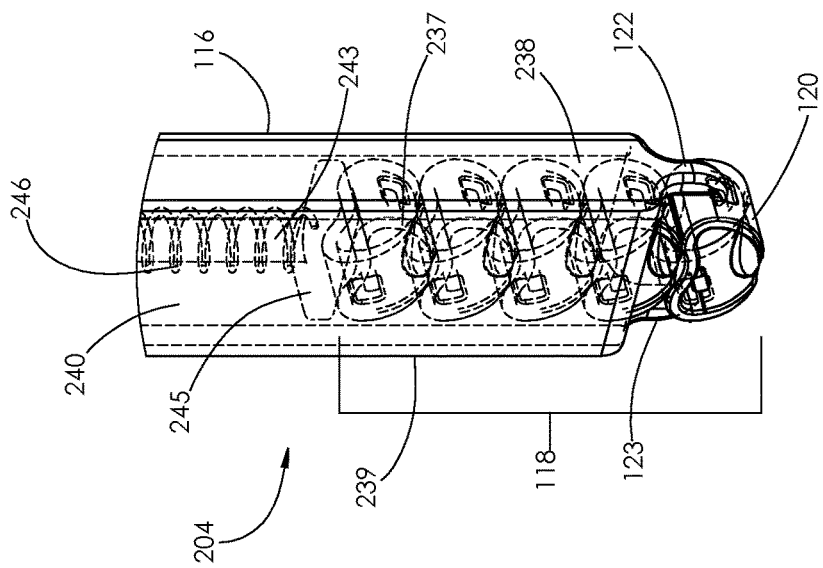
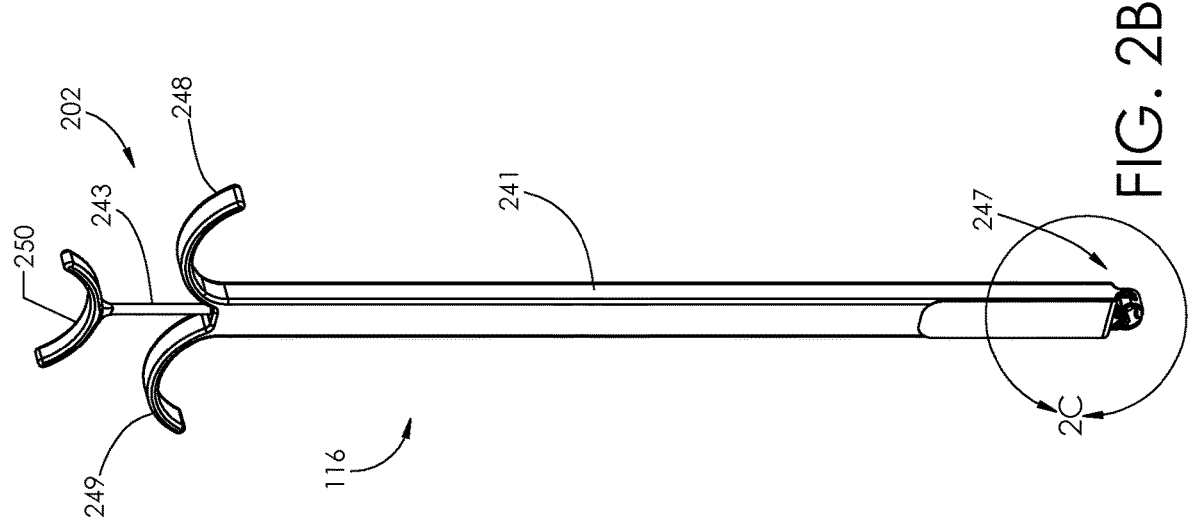
FIG. 2C
FIG. 2B

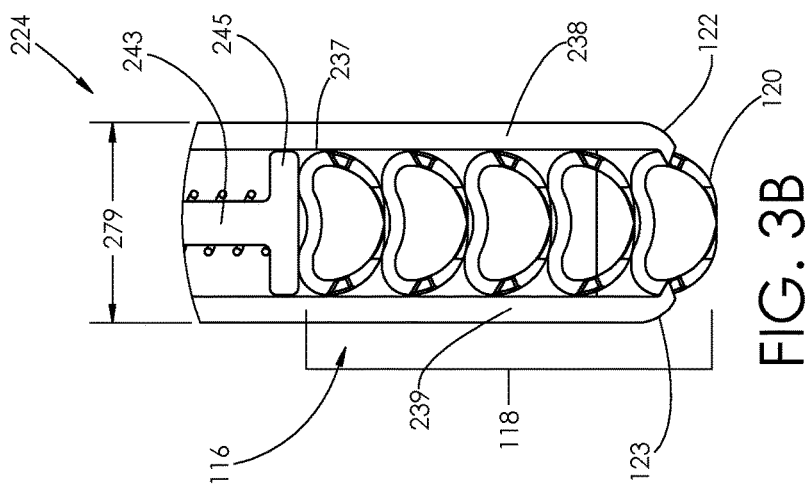
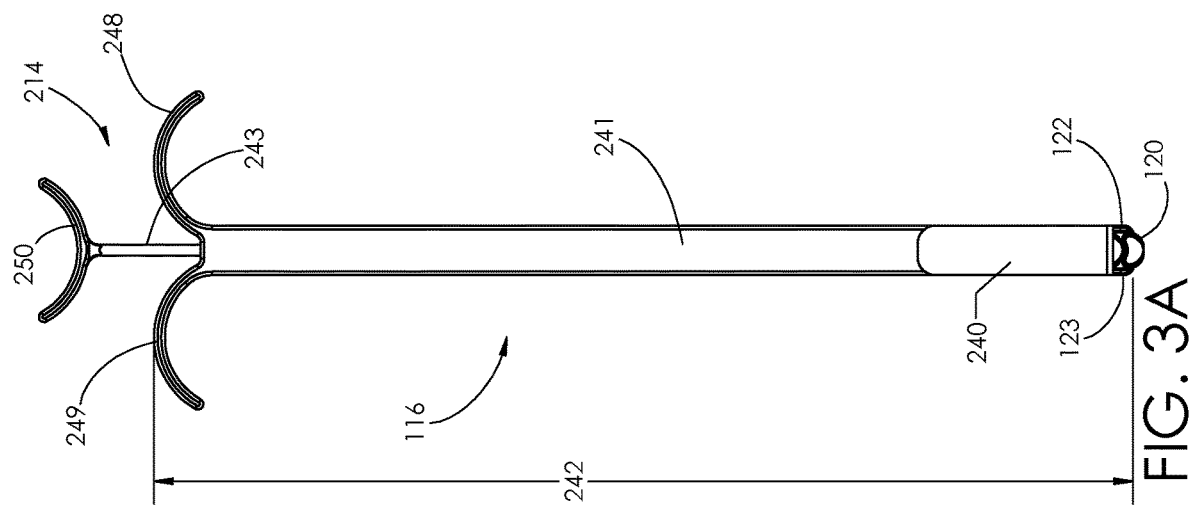

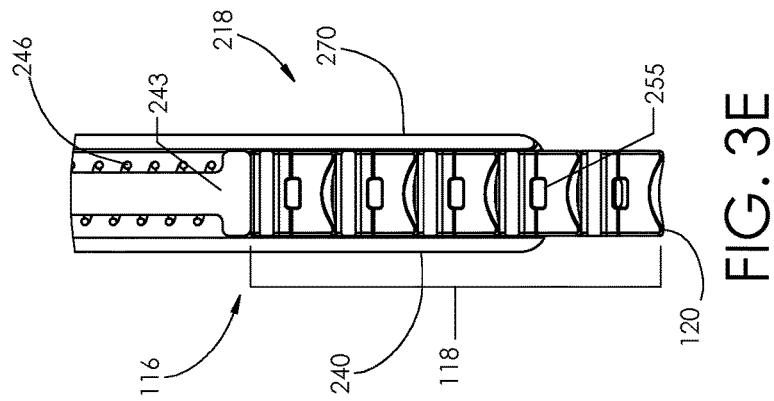
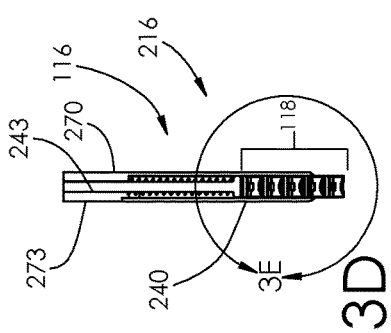
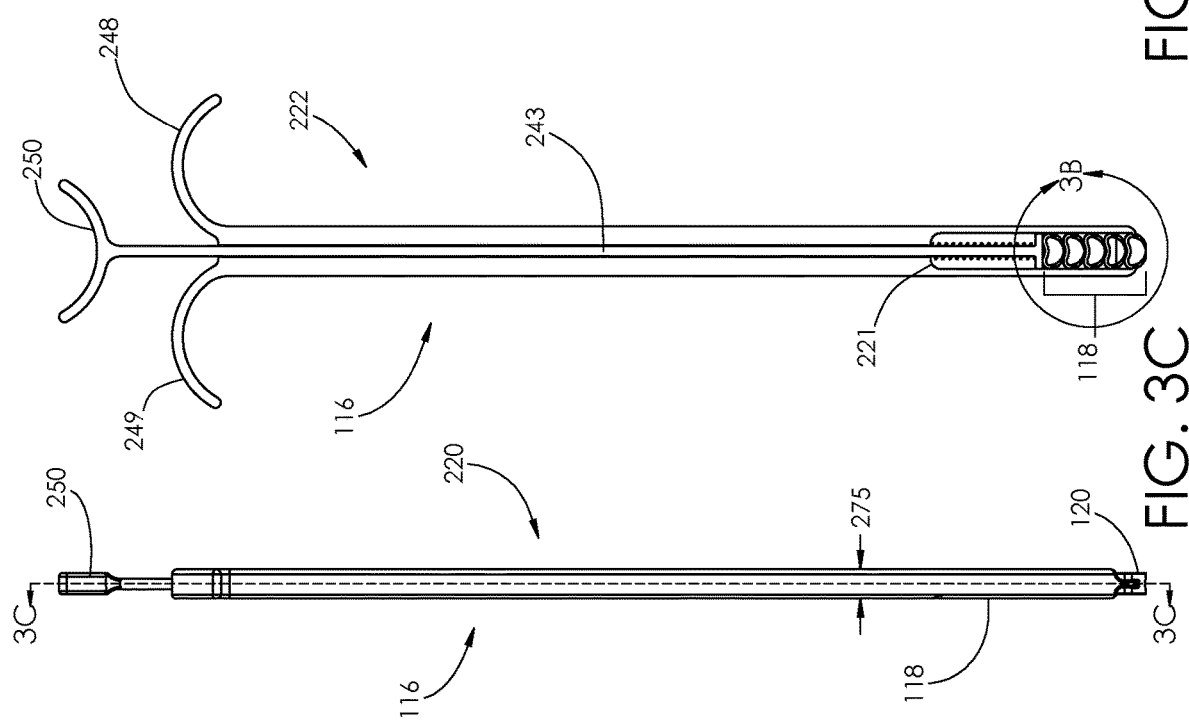
FIG. 3E
FIG. 3D
FIG. 3C

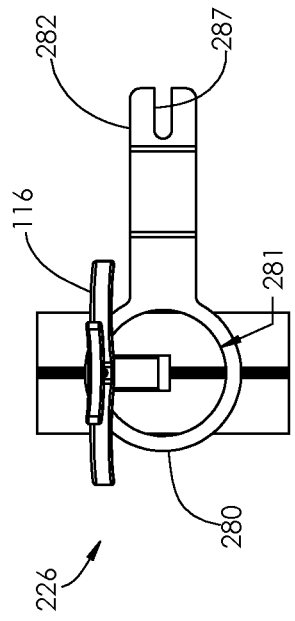
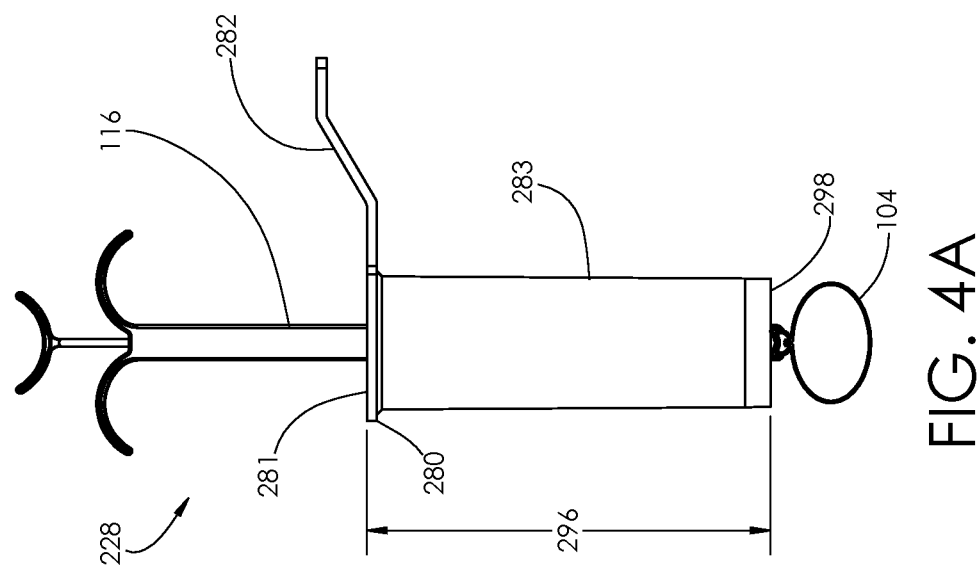

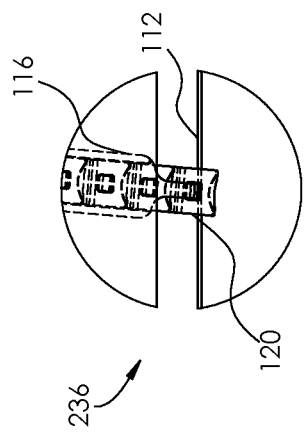
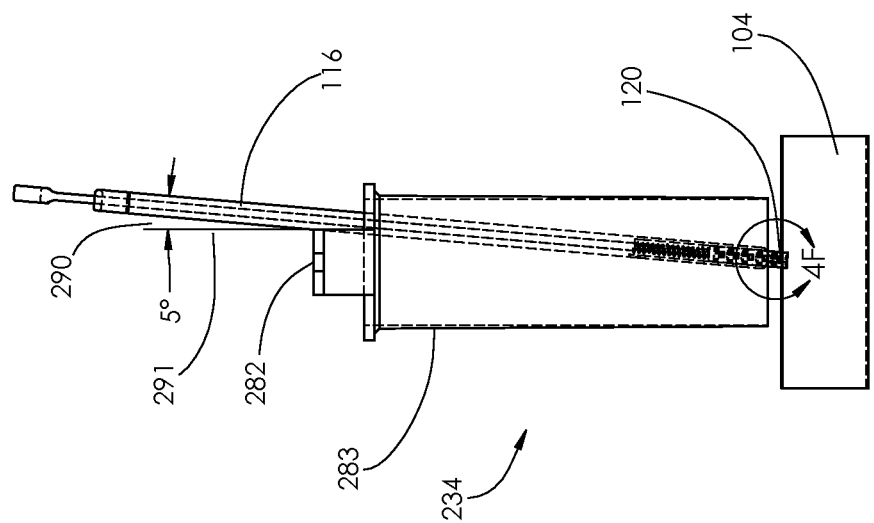

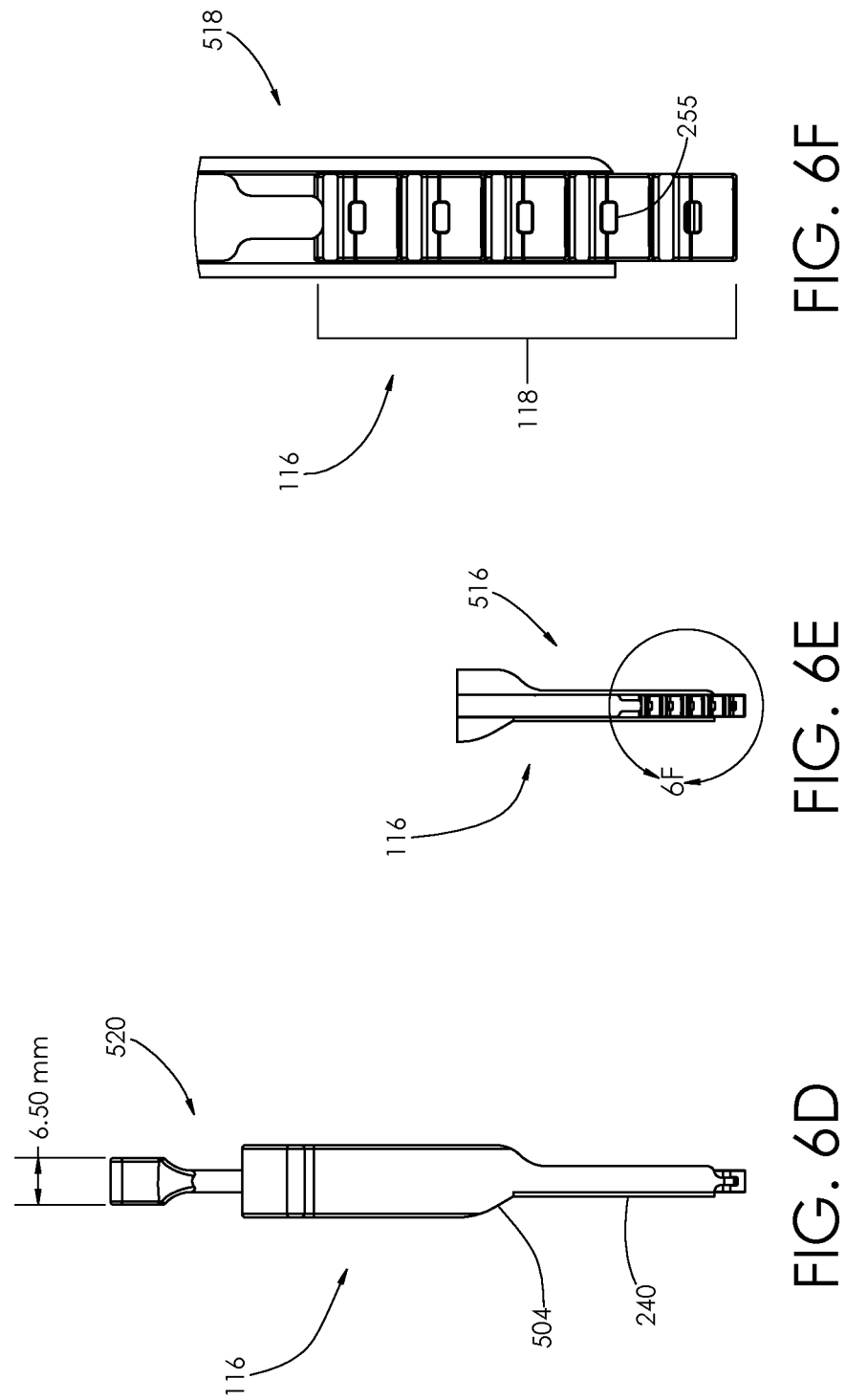

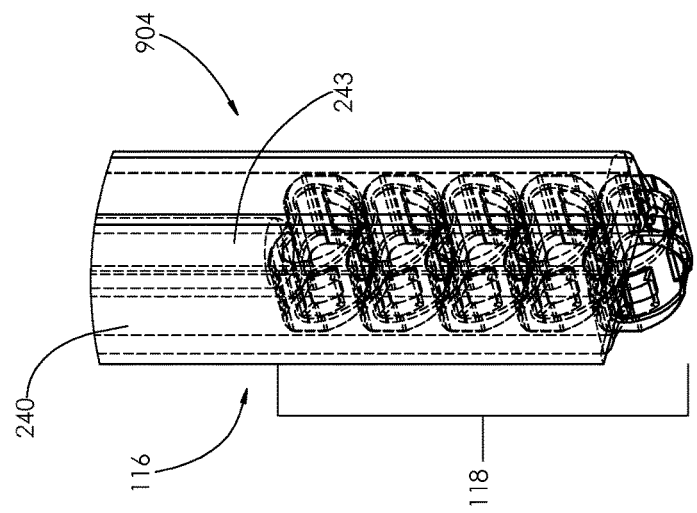
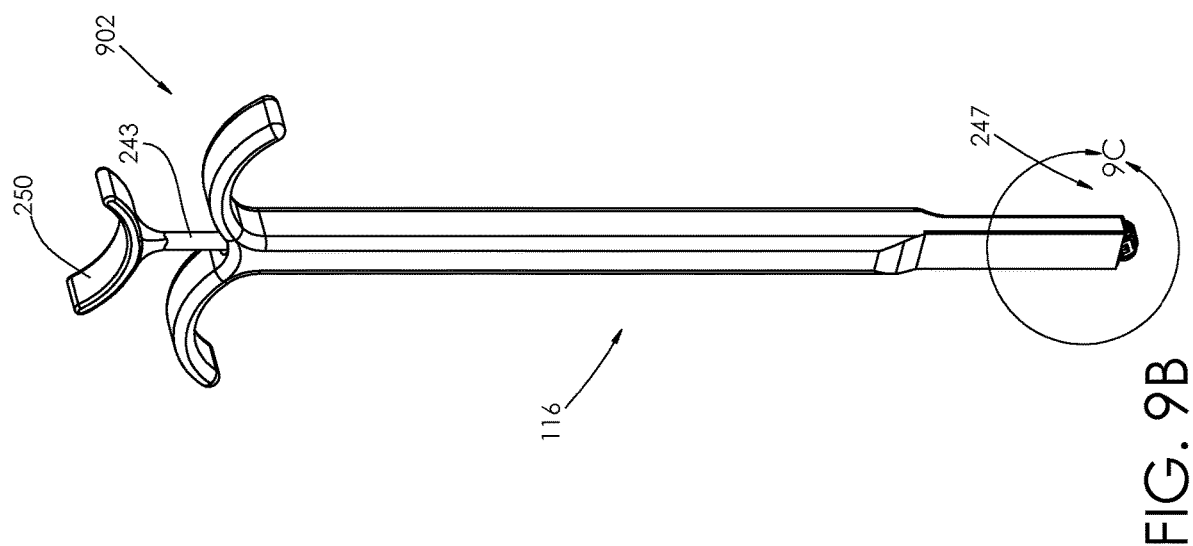
FIG. 9C
FIG. 9B

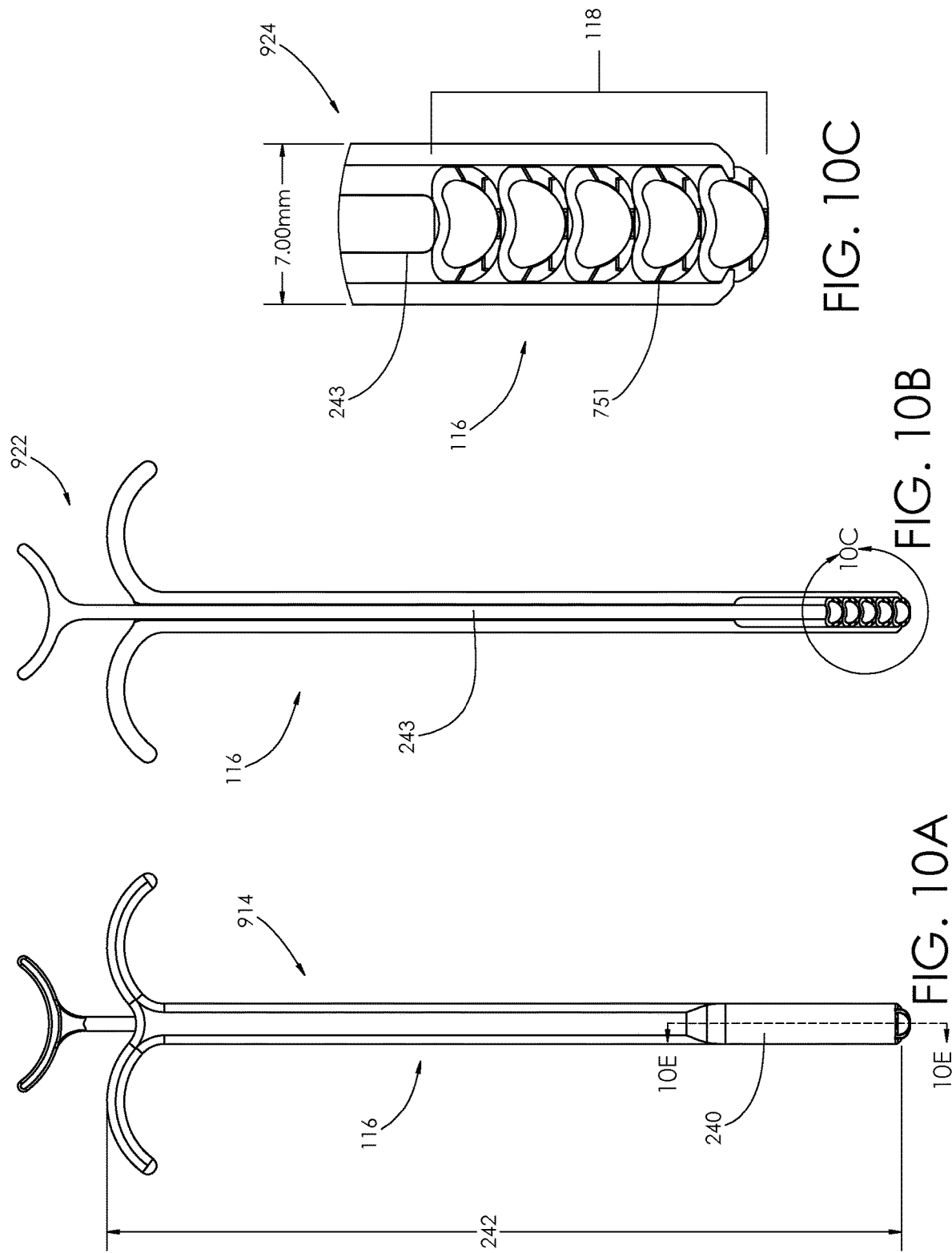

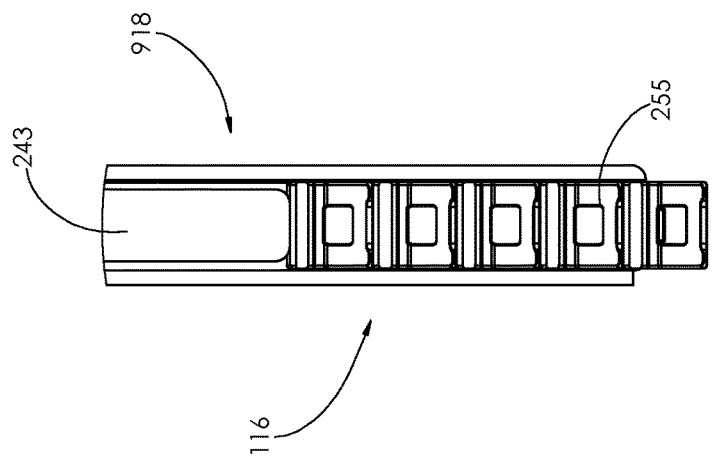
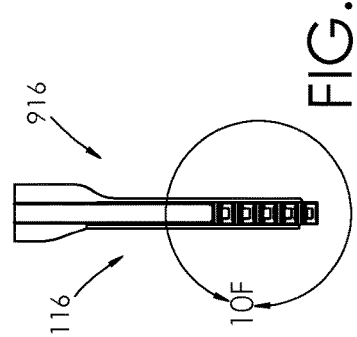
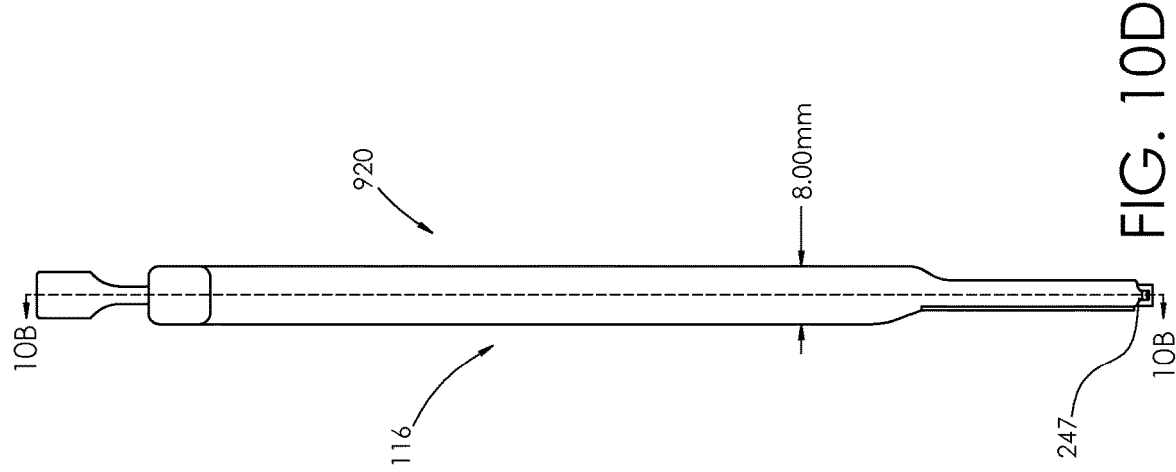
FIG. 10F
FIG. 10E
FIG. 10D

BIOABSORBABLE CLIPS AND APPLICATOR FOR TISSUE CLOSURE

CROSS REFERENCE TO RELATED APPLICATIONS

The present application claims priority to U.S. Provisional Patent Application No. 61/878,298, filed Sep. 16, 2013, entitled "BIOABSORBABLE STAPLES AND APPLICATOR FOR TISSUE CLOSURE," the entire disclosure of which is hereby incorporated by reference in its entirety.

STATEMENT OF GOVERNMENT SUPPORT

This invention was made with government support under TR000128 awarded by the National Institutes of Health. The government has certain rights in the invention.

FIELD

The present disclosure relates to surgical clips and surgical clip applicators used in tissue closure.

BACKGROUND

The brain and spine are covered with a tough outer membrane called the dura mater, or dura. During surgical procedures, e.g., spinal surgery, the dura mater may be opened intentionally or inadvertently. Such an opening is called a durotomy or dural tear. Dural tears requiring closure or repair have been reported to occur in a significant percentage of surgical procedures. In some approaches, sutures are used to repair or close the dura. Durotomies must be closed prior to closing the skin. Failure of the closure can result in persistent cerebrospinal fluid (CSF) leakage, for example. This leakage may result in wound breakdown, spinal headaches, infection, meningitis, and other consequences.

Minimally invasive surgeries (MIS) are becoming more commonly used during surgical procedures, e.g., to treat a variety of pathologies including herniated discs, spinal stenosis, synovial cysts, spondylolisthesis, deformity, intra-dural tumors, etc. Such procedures use smaller incisions to decrease intraoperative blood loss, reduce tissue disruption, decrease postoperative pain, and decrease lengths of hospital stays, for example.

Minimally invasive surgeries make use of smaller ports and result in less tissue disruption than traditional procedures. However, should a durotomy occur using a minimally invasive surgery, closure of that durotomy can become extremely difficult or impossible due to the small size of the incision. For example, in the setting of minimally invasive spine surgery, the ability to close a durotomy may be compromised when suture material cannot be manipulated sufficiently to achieve tight closure. Thus, due to the physical limitations of small working areas, repair of a durotomy may be technically difficult and time-consuming when using conventional suture and knot-tying techniques.

In order to overcome these technical difficulties resulting from minimally invasive surgeries, metal clips or staples, such as titanium clips, delivered via a suitable applicator may be crimped or bent from an open position into a closed position around the tissue edges to close a hole in a tissue such as a durotomy. However, in such approaches, it is necessary to place the clips close together along a dura tear in order to close the tissue since such clips may too thin to cover and hold significant lengths along the tissue break.

Further, use of metal clips or staples either results in a permanent foreign body left in the tissue or a second surgical intervention to remove the staples. Staples left in the tissue interfere with postoperative imaging since metal clips result in undesirable artifacts in radiographic imaging such as magnetic resonance imaging (MRI) and computed tomography (CT) scans.

SUMMARY

The present disclosure is directed to surgical clips and surgical applicators that may be used in performing rapid tissue closure in either minimally invasive surgeries or traditional open procedures. In particular, the surgical clips described herein are intended for use in closing durotomies, particularly durotomies resulting from minimally invasive surgeries.

A surgical applicator is used to deliver the clips down a small opening, thereby obviating the need for sutures and knot tying to close the durotomy. An array of stacked surgical clips is to be loaded into a chamber or reservoir of the surgical applicator. A force is applied to the center of the top of a clip located at a tip of the surgical applicator. The sides of that clip are held at the tip of the applicator such that the mouth of the clip opens around the everted tissue edges of the dura. Upon release of the clip from the applicator, the clip grasps the everted edges, pulling the edges towards one another, closing the tear in the tissue. The push rod can then engage the next clip in the array so that the next clip is pushed into position to be opened at the mouth of the applicator for a subsequent application.

Since everted tissue edges are grasped by the surgical clip in such an approach, a risk of adhesion to the underlying spinal cord may be potentially reduced. Further, by applying a force to open such a surgical clip from a closed, resting state to an intermediate open state and then releasing the force to permit the clip to close to its resting state around the dural tissues, a greater amount of control may be conferred to the final closed state of the clip around the tissues to provide pressure on the dura leaflets for maintaining closure of the durotomy.

In this way, closure of the dura using a small bioabsorbable clip to grasp but not penetrate the tissue edges and maintain tension until the tissues heal may be applied quickly, easily, and in rapid succession by using an applicator. Such an approach may potentially increase speed and ease of clip application, decrease the risk of CSF leakage, decrease intradural adhesions due to non-penetration of the clip, reduce risk of adhesion to the underlying spinal cord, minimize dural exposure, and decrease expensive operative time. Further, such an approach may also be used in other surgical arenas where reapproximation is desired; including, for example, cranial surgery for closure of the dura, general surgery for closure of hollow organs, urologic surgery for closure of the bladder, closure of uereters and other tubular structures, and gynecological procedures for closure of reproductive structures.

Disclosed herein is a surgical clip that includes opposing sides extending from a top portion. The opposing sides terminate at tips positioned below the top portion. The resting position of the clip is its closed position, and in the closed position, the tips are set at a first distance apart. Each side has a cut-out (or hole or aperture) opposite one another. Each cut-out is fully surrounded by the side and does not extend to the top or tips. Each cut-out is configured to engage an inwardly turned hook at the end of a clip array or clip applicator such that the sides bend outwardly away from each other when pressure is applied on the top portion of the clip, thereby placing the clip in an open position. In the open position, the distance between the tips is greater than the distance between the tips in the open position. In addition, the width of the clip is at least 25% of the length of the clip (length is the dimension from the end of the first side to the end of the second side, while width is the dimension of the clip perpendicular to the length). Each tip is made up of at least two points. Each point converges to a point towards the opposing point on the other side to form a barb-like feature.

In additional examples, the top portion can be flat or concave and/or may include a cut-out or aperature. The sides can be straight, flat, or convex. The sides can also comprise a flat portion coupled to the top portion by a curved top junction and coupled to the tip via a curved bottom junction. In this case, the flat portion can be perpendicular to the top portion in the closed position and at an angle greater than 90° in the open position. In still more examples, the clip may be made of a bioabsorbable and/or radiolucent material. Alternatively, the height of the clip may be less than the width and length of the clip.

Disclosed herein is an array of surgical clips. The array comprises two or more of the clips described above and a chamber housing the clips. The chamber is small enough to maintain the sides of all the clips oriented in the same direction, but large enough to allow movement of the clips in the direction of the tips of the clips. The clips are vertically stacked along a central axis extending through the center of the top portion and a center midpoint between the first and second tips of each clip. The clips in the array can also be in physical contact with one another.

Disclosed herein is a surgical clip applicator. The applicator includes a clip array as described above that has a chamber with an open end, inwardly facing hooks distal to the top clip in the array, and a push rod configured to apply pressure to the top clip in the array. The hooks can be coupled to the open end of the chamber. Alternatively, the hooks can be coupled to the body of the applicator. The applicator can also have a transparent view window in a wall of the chamber. The view window extends from the open end of the chamber. The distance is such that all the clips in the chamber can be visualized. The view window is perpendicular to the opposing interior walls of the chamber.

It should be understood that the summary above is provided to introduce in simplified form a selection of concepts that are further described in the detailed description. It is not meant to identify key or essential features of the disclosed subject matter, the scope of which is defined uniquely by the claims that follow the detailed description. Furthermore, the disclosed subject matter is not limited to implementations that solve any disadvantages noted above or in any part of this disclosure.

BRIEF DESCRIPTION OF THE SEVERAL VIEWS OF THE DRAWINGS

FIGS. 2A-12F show scaled drawings of example surgical clips and example surgical clip applicators in accordance with the disclosure.

DETAILED DESCRIPTION

Figure 1:
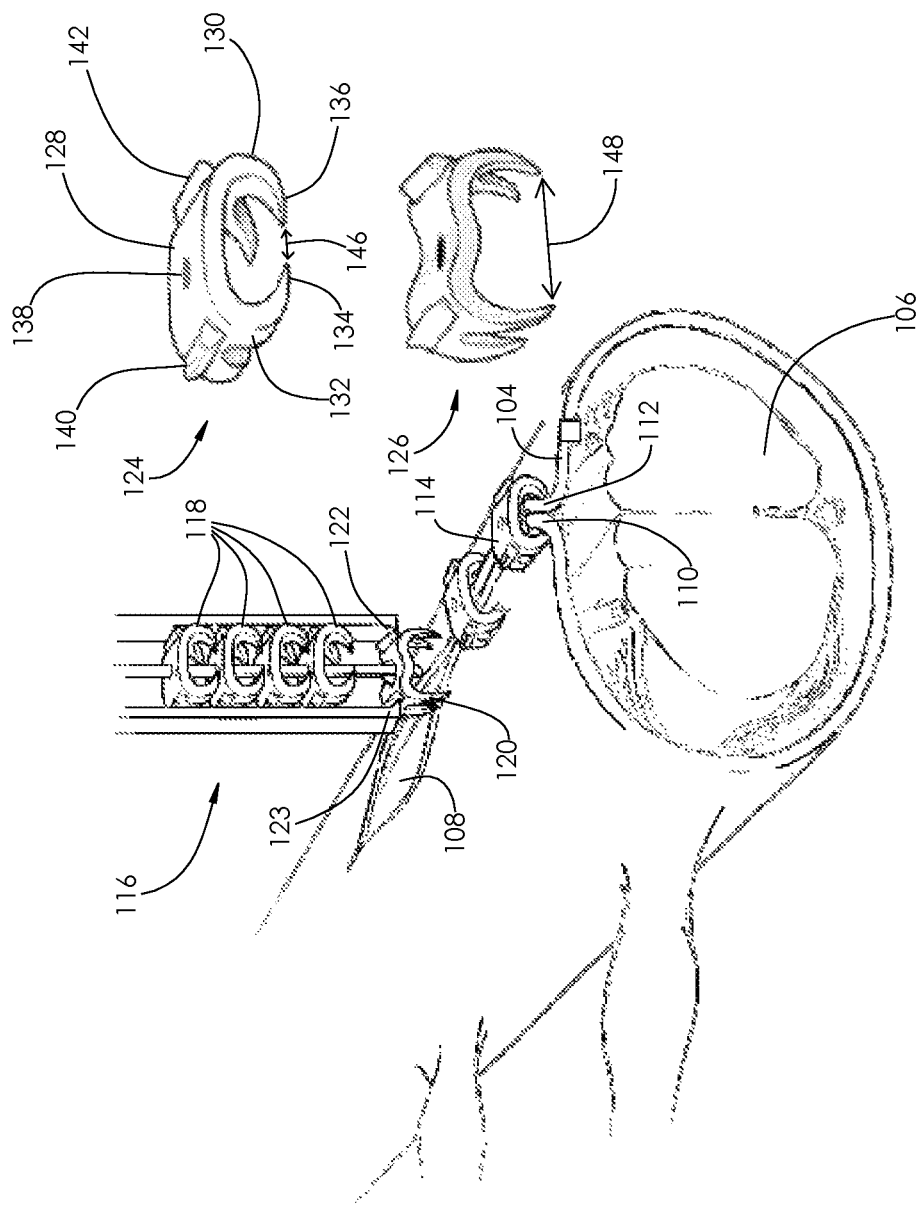
FIG. 1 shows an illustration of a surgical applicator applying example surgical clips to close a durotomy.

The following description relates to bioabsorbable surgical clips and surgical applicators for performing rapid water-tight tissue closure in minimally invasive or traditional open procedures. For example, as illustrated in FIG. 1, a surgical applicator 116 may be used to deliver one or more surgical clips, e.g., clips 118, to assist in tissue closure. In FIG. 1, a dural tear or durotomy 108 is shown in the dura mater 104 around a spinal cord 106. As remarked above, the dura mater is a tough outer membrane covering the brain and spinal cord which may be opened intentionally or inadvertently during surgical procedures. The clips disclosed herein can be interchangeably referred to as staples and vice versa.

The surgical clips may be composed of any material including any suitable bioabsorbable or resorbable material. The terms bioabsorbable and resorbable are used herein to mean dissolving inside the human body after a period of time. In some examples, the bioabsorbable material may be chosen based on a time duration at which the material dissolves. For example, the bioabsorbable material may have the property that it does not substantially dissolve within seven days after installation along the tissue but dissolves anytime after one week while maintaining structural integrity before then. For example, the bioabsorbable material may comprise a biocompatible, bioabsorbable polymer such as Poly-L-Lactic Acid/Poly glycolic acid (PLLA/PGA), Polycapralactone, or some combination thereof. By using a bioabsorbable material, no permanent foreign body is left in the tissue following surgery. Further in some examples, the clip may be composed of a material that is radiolucent, e.g., invisible or transparent to x-rays, as well as bioabsorbable. For example, the surgical clips may be composed of a suitable material which is radiolucent and bioabsorbable so that substantially no undesirable artifacts from the clips appear in radiographic imaging e.g., in magnetic resonance imaging (MRI) and computed tomography scans (CT). Further, by using a bioabsorbable and radiolucent material, surgical clips with a wide footprint may be used to cover a greater length along the tissue thereby potentially decreasing a number of clips needed to reliably seal the tissue in a water tight fashion.

As illustrated in FIG. 1 at 124, a surgical clip used to close a durotomy may comprise a first side 132 and a second side 130, where the second side 130 opposes the first side 132. The first and second opposing sides 132 and 130 extend from a top portion 128 of the clip and terminate at first and second tips positioned below the top portion 128. For example, the first side 132 is coupled to and extends from top portion 128 and terminates at a first tip 134 positioned below the top portion 128. Likewise, the second side 130 is coupled to and extends from top portion 128 and terminates at a second tip 136 positioned below the top portion 128. In an installed, closed position, the tips 134 and 136 of the surgical clip grasp but do not penetrate or pierce everted tissue edges. For example, in FIG. 1 surgical clip 114 is shown in an installed position along the durotomy 108 grasping everted tissue edges 112 and 110. The surgical clips may include a variety of features and may have a variety of shapes and dimensions, examples of which are described below with reference to the scaled drawings of FIGS. 2A-12F. For example, the clip may have a length in a range from 3-5 millimeters (mm), a height in a range of 3-5 mm, a width in a range of 3-5 mm, and a diameter (if cylindrically shaped) in a range of 3-5 mm. In some examples, the top portion 128 of the clip may include an aperture 138, slots, and/or other features used to achieve a particular bending moment of the surgical clip. For example, as described in more detail below, sides of the surgical clip may be temporarily bent outward by applying a force to the top portion of the clip while holding the sides in place to install the clip over everted tissue edges. A size of a slot or aperture or a thickness of the top portion of the clip may be adjusted so that the clip confers an optimal amount of force to grasp the tissue while maintaining the ability to be temporarily opened via engagement with features on an end of the surgical applicator during an installation of the clip. For example, the clip may be designed to withstand at least 10 cmH₂O pressure (e.g., prostrate pressure) without leakage and may, in some examples, be designed to withstand 20 cmH₂O (e.g., standing lumbar pressure) without leakage. Further, the material selected may be based on a desired elasticity for applying a predetermined holding force to the tissue for a predetermined duration following installation of the clip around everted tissue edges.

The clip may include features which are configured to engage with the surgical applicator to assist in installation of the clip around edges of a tissue break. For example, the surgical clip may include cut-outs, notches, tabs or other suitable features which engage protrusions at a tip of the surgical applicator, e.g., which engage protrusions 122 and 123 of surgical applicator 116 shown in FIG. 1. The example clips shown in FIG. 1 include tabs extending outwardly from the first and second sides of the clip. For example, a tab 140 is shown extending outwardly from first side 132 and may be configured to engage with protrusion 123 of the applicator 116 and tab 142 is shown extending outwardly from second side 130 and may be configured to engage protrusion 122 of the applicator. However, in other examples, such tabs may be omitted or other alternative engagement features may be included on the opposing sides of the clip. In some examples, the opposing ends of the clip may include locking features which assist in holding the clip in a closed position after an installation of the surgical clip around everted tissue edges. For example, a barb or other suitable feature may be included on the clip extending inwardly from a first side of the clip where an end of the barb is configured to engage with an aperture included in a second side of the clip opposing the first side.

As illustrated in FIG. 1, a stack of surgical clips 118 may be loaded into the surgical applicator 116 for quick successive delivery of surgical clips to grasp everted tissue edges, e.g., the bent and interfacing tissue edges 112 and 110, to close the durotomy. For example, as shown in FIG. 1, an installed surgical clip 114 grasps but does not penetrate or pierce the everted edges of the dura thereby holding the edges together. Surgical applicator 116 may be used to deliver the clips down a small opening during minimally invasive procedures thereby potentially obviating the need for sutures and knot tying to close the dura. In one example approach, an array of stacked surgical clips 118 may be loaded into a chamber or reservoir of the surgical applicator and a downward force from a push rod in the chamber may be used to push the center of a clip located at a tip of the surgical applicator, e.g., clip 120 shown in FIG. 1, while the sides of that clip are firmly held at the tip causing the mouth of the clip to open around the everted tissue edges 110 and 112 of the dura. To release the clip, the center push rod may be retracted allowing the clip to grasp and reapproximate the two dural edges 110 and 112. The center push rod can then retract further to engage the next clip in the reservoir so that the next clip is pushed into position to be opened at the mouth of the applicator for a subsequent application to the everted tissue edges. It should be understood that the use of a push rod to eject the clip is exemplary in nature and that any other suitable pusher or ejector feature may be included in the clip applicator. Further, the term "push rod" as used herein may refer to any such suitable pusher or ejector feature of the applicator used to deploy the clips.

The surgical clips have a closed resting configuration which can be substantially the same before and after installation along the tissue edges. During installation with the surgical applicator, the surgical clips have an intermediate open state formed by engagement of the clip with a tip of the surgical applicator during the installation of the clip. By applying a force to the top of the clip while sides of the clip are engaged with the tip of the surgical applicator, a reversible deformation of the clip from a closed resting position to an intermediate open position may occur. This deformation is recoverable upon removal of the force applied to the top of the clip after the clip is positioned around the tissue edges so that the clip returns to its closed resting position to grasp the everted edges when the force is removed from the clip.

FIG. 1 shows an example clip in a closed resting state at 124 and in the intermediate open state at 126. In the closed resting state there is a first distance 146 between the first and second tips 134 and 136. In this closed position, the first distance may chosen so as to provide a sufficient amount of space between the tips 134 and 136 to accommodate a thickness of the everted tissue edges to which it is to be applied (e.g., enough space to accommodate twice the thickness of the dura) while maintaining sufficient gripping force on the everted tissue edges after application. The first side 132 and the second side 130 of the clip are configured to engage the clip applicator such that, when the clip applicator is used to apply downward pressure to the top portion 128 of the clip, the first and second sides bend outwardly away from each other thereby increasing the distance between the tips to a second distance 148 greater than the first distance 146 so that the clip is temporarily deformed to an open position for installation around the tissue edges. In some examples, this second distance 148 may be a predetermined distance, e.g., at least 3 mm, achieved via forces applied to the clip from the clip applicator.

By applying a force to open such a surgical clip from a closed, resting state to an intermediate open state and then releasing the force to permit the clip to again close to its resting state around the dural tissues, a greater amount of control may be conferred to the final closed state of the clip around the tissues to provide an optimal pressure on the dura leaflets for maintaining closure. For example, the grasping force of the closed resting state of such a clip may be tailored to a specific type or thickness of tissue to which it is to be applied.

FIGS. 2A-12F described below show scaled drawings of various example embodiments of surgical clips and surgical clip applicators. Each of the drawings shown in FIGS. 2A-12F is drawn to scale and the example numerical dimensions shown in these figures are in millimeters (mm). Further, like numbers used throughout the figures correspond to like elements.

Turning to FIGS. 2A-4F, a first example embodiment of a surgical applicator 116 and surgical clip 124 is shown from various perspectives and cross-sections. At 206, 208, 210, and 212 in FIG. 2A various viewpoints of the first example embodiment of a surgical clip 124 are shown. In particular, a front face view of an example clip 124 is shown at 206, a side view of clip 124 is shown at 208, a bottom view of clip 124 is shown at 210, and a perspective view of clip 124 is shown at 212.

Clip 124 comprises a concave top portion 128 with opposing rounded convex sides 130 and 132 extending therefrom. In particular, a first side 132 is coupled to top portion 128 via a rounded junction 251 and curves inwardly from junction 251 to a tip 134 positioned below top portion 128. Likewise, a second side 130 is coupled to top portion 128 via a rounded junction 252 and curves inwardly from junction 252 to a tip 136 positioned below top portion 128. A thickness of each tip of the opposing tips 136 and 134 tapers or decreases in a direction toward the opposing tip so that each tip of the opposing tips 136 and 134 converges to a point in a direction towards the opposing tip. The concave top portion 128 curves toward the interior of the clip in the center of the top portion so that a minimum height of the clip occurs at the center of the top portion. The convex opposing sides 130 and 132 and the rounded junctions 251 and 252 coupling the sides 132 and 130 to the top portion form a heart-shaped face as seen in view 206 wherein each opposing side forms opposing "C-shapes" which are coupled together via the concave top portion 128.

Each of the first and second tips 134 and 136 converges to a point in a direction towards the opposing tip. For example, tip 134 is comprised of a first point 260 and a second point 262 and tip 136 comprises is comprised of a first point 259 and a second point 261. Each point of a tip converges in thickness and width to a point facing an opposing tooth on the other tip. For example, a width and thickness of tooth 260 on tip 134 decreases in a direction toward the opposing tooth 259 on tip 136 and a width and thickness of tooth 262 on tip 134 decreases in a direction toward the opposing tooth 261 on tip 136. Teeth 259 and 261 on tip 136 likewise converge to the opposing teeth on tip 134 so that an aperture 263 is formed in the bottom of the clip between teeth of the tips. In some examples, this aperture 263 may have a circular shape with a predetermined diameter, e.g., a diameter of 2.5 mm. However, it should be understood that the aperture formed between the teeth of the tips on the bottom of the clip may have any suitable diameter or shape, e.g., oval, rectangular, etc. The points may be used to hold everted edges of tissue in place while not penetrating and not piercing the tissue when repairing a durotomy, for example. One of skill in the art in light of this disclosure would understand how to make tips 134 and 136 of sufficient sharpness to grasp but not penetrate or pierce everted edges of a tissue such as a dura without undue experimentation.

Example clip 124 further includes cut-outs in each opposing side of the clip for engagement with opposing protrusions 122 and 123 at a distal end 247 of the clip applicator 116. For example, first side 132 includes a cut-out 255 forming a rectangular aperture or hole within a center of the first side 132. Likewise, second side 130 includes a cut-out 256 forming a rectangular aperture or hole in the center of the second side 130. These cut-outs in the sides of the clip may be sized and shaped so that the opposing protrusions 123 and 122 at the end 247 of the applicator lock the clip in place at the end of the applicator as exemplified with clip 120 at 204 in FIG. 2C.

The example clip 124 has a height 254 extending in a direction from a midpoint of the opposing tips 134 and 136 towards the top portion 128, a length 253 extending in a direction from first side 132 towards second side 130, and a width 299 extending from a front of the clip towards the back of the clip in a direction perpendicular to length 153. In this example, the height 254 is less than the length 253 and the height is substantially the same as the width 299. For example, the length may be approximately 5 mm and the height and width may both be approximately 3 mm; however, it should be understood that these dimensions are provided as examples and any suitable height, length, and width may be used. The cut-outs 255 and 256 may be located in a center of the sides of the clip and may have a width 257 of approximately 1 mm along a direction of width 299 and may be offset from the face of the clip by an amount 258 which may be approximately 1 mm, for example. Again, it should be understood that these dimensions are provided as examples and any suitable dimensions for the cut-outs may be used.

Figure 2A:
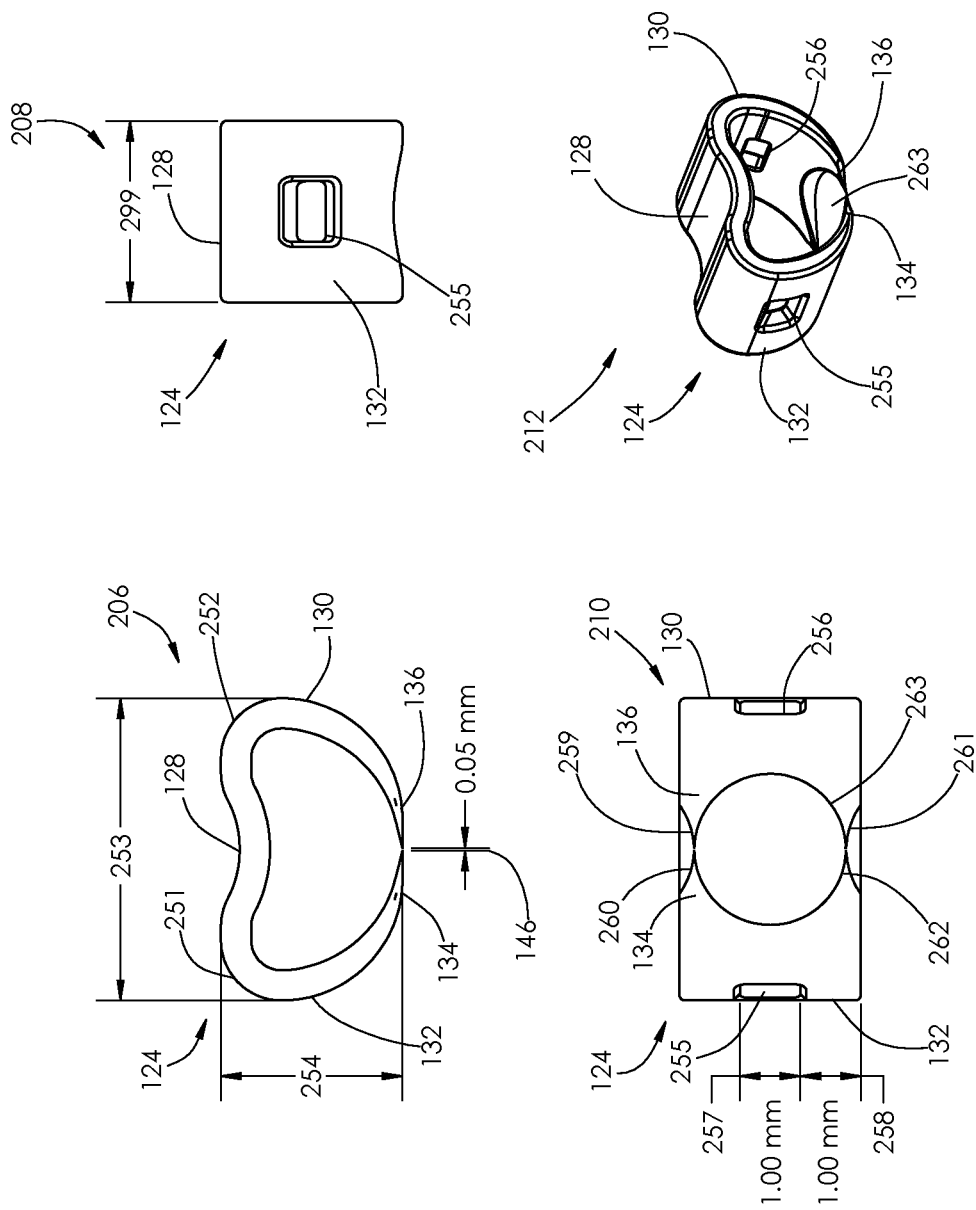
Figure 4D:
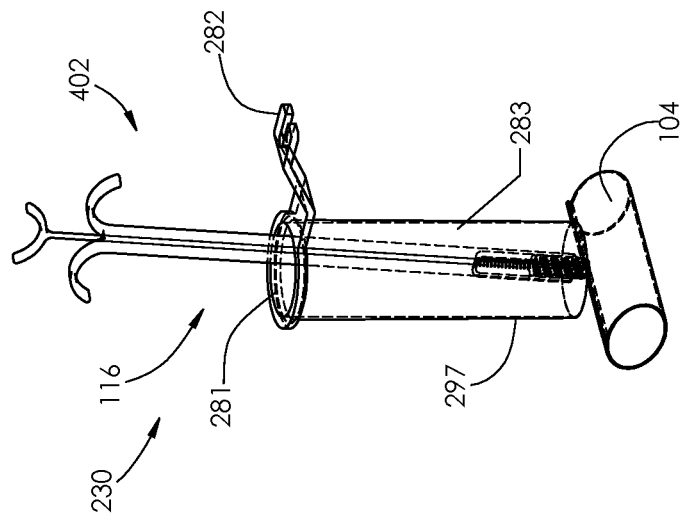
Figure 4C:
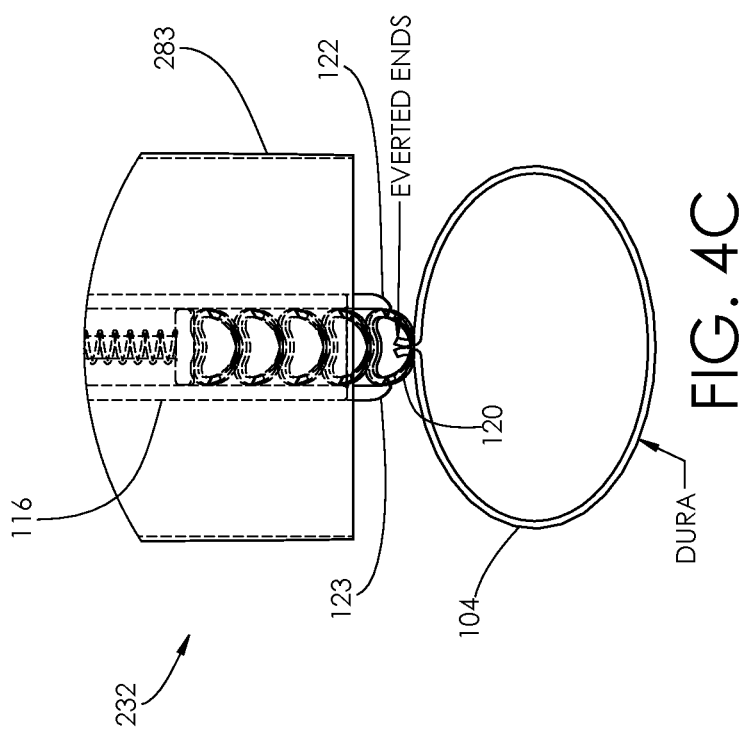

The surgical clip 124 is shown in views 206, 208, 210, and 212 in FIG. 2A in a closed resting position with a first distance 146 between opposing tips 134 and 136. For example, this first distance 146 between the tips may be approximately 0.05 mm when the clip is in its resting closed state. A length of this first distance 146 may be based on a type and thickness of tissue to which it is to be applied. For example, the first distance 146 may be greater for applications on a thicker tissue.

Though not shown in FIG. 2A, in some examples, the top portion 128 may be substantially flat when the clip is in the resting state (e.g., as shown in FIG. 1), but may become concave or temporarily bent inward during a transitional intermediate open state of the clip during installation of the clip using clip applicator 116. In particular, protrusions 123 and 122 of clip applicator 116 may engage cut-outs 255 and 256 when the clip is positioned at the distal end 247 of the applicator to hold the clip in place while a force is applied to the top of the clip so that the distance between the tips of the clip increase to a second distance greater than the first distance 146, e.g., greater than 0.05 mm, so that the tips of the clip are opened for installation of the clip around everted tissue edges. This second distance may be a distance of at least a predetermined amount, e.g., at least 3 mm.

Various views and cross-sections of an example surgical applicator are shown at 202, 204, 214, 216, 218, 220, 222, and 224 in FIGS. 2A-3E. In particular, at 202, a perspective view of example surgical clip applicator 116 is shown. At 204, a detailed view is shown of a distal end 247 of the applicator 116 at the region F shown in view 202. The view 204 is shown at a scale of 4:1 relative to the view shown at 202. At 214 a front view of applicator 116 is shown. At 216, a detailed view is shown of cross-section A-A shown in view 214. View 218 shows a detailed view of the cross-section A-A of the region B shown in view 216, where view 218 is shown at a scale of 4:1 relative to view 216. View 220 shows a side view of applicator 116. View 222 shows a cross-sectional view along cross-section C-C from view 220. View 224 shows a detailed view of region D shown in view 222 and is shown at a scale of 4:1 relative to view 222. Further, the views 206, 208, 210, and 212 of clip 124 are drawn at a scale of 8:1 relative to view 202 of applicator 116.

With reference to views 202, 204, 214, 216, 218, 220, 222, and 224 shown in FIGS. 2A-3E, the surgical applicator 116 comprises an elongated body 241 defining a chamber with an open end 247 within which a push rod 243 is contained. The push rod 243 extends away from the open end 247 of the surgical clip applicator and terminates at a thumb pusher element 250. The thumb pusher element 250 comprises a curved handle shaped to fit a thumb of a user. The clip applicator further includes two opposing finger grasping elements 248 and 249 coupled to the elongated body 241. For example, a user may grip the finger grasping elements 248 and 249 with two fingers and apply a downward force to the thumb pusher element 250 to urge the push rod downward toward the distal end 247 in order to apply a force to one or more clips in the chamber of the applicator.

An array or stack of surgical clips 118 is included within a chamber or reservoir within the walls of the elongated body 241 of the applicator. In the array of stacked clips 118, the stacked surgical clips are vertically stacked along a central axis extending through a center of the top portions and a center midpoint between the first and second tips of each surgical clip in the array and the first and second opposing sides of each clip are orientated in the same direction as the first and second opposing sides of the other clips in the plurality of stacked surgical clips.

In some examples, the array of stacked clips may be loaded into the chamber of the surgical applicator as a group rather than individually. For example, a user may obtain a package of a predetermined number of pre-stacked and pre-aligned surgical clips, e.g., including five or more individual clips stacked one on top of the other and oriented in the same direction, and may load this package of clips into the surgical applicator, e.g., via an entry point comprising an opening at a top end of the applicator when the push rod 243 is removed from the chamber. As another example, an array of surgical clips may be preloaded into the applicator so that an end user receives a fully assembled pre-packaged applicator including a pre-loaded quantity of clips loaded within the chamber. Such a pre-packaged surgical clip applicator may have any suitable number of clips contained therein, e.g., 5, 10, 15, or 30 clips per applicator. The number of clips included in an applicator may depend on a particular surgical application. Though five clips are shown in the array of stacked clips in the figures, any suitable number of clips may be included in a clip array. For example, the number of clips included in a clip array may depend on a particular surgical application or a length of the tissue tear to which the clips are to be applied. Such a pre-packaged pre-loaded surgical clip applicator may be sterilized and suitably wrapped and, in some examples, may be disposable after use and may include labeling which indicates various parameters associated with the surgical applicator and clips therein such as dimensional information, disclaimer information, clip material composition, etc.

Different sizes of the applicator may be available depending on a quantity of clips desired (e.g., an applicator may house 5-30 clips). For example, the applicator may come in different lengths depending on type of surgery to be performed and the tissue on which the surgery will be performed. A short handle applicator may be used for open surgeries while a longer handle applicator may be used for deeper, smaller portals generated by minimally invasive surgical procedures. For example a height 242 of the applicator 116 may be in a range of 125-150 mm (~5-6 inches) for minimally invasive procedures. The applicator may be used by right or left-handed male and female neurosurgeons and may utilize activation mechanisms that are standard or familiar to neurosurgeons. For example, the activation mechanism of the applicator may utilize a pistol grip design, a syringe plunger-type design, a looped-end forcep design, etc. Further, the applicator may be activated by fingers of a user rather than whole-hand activation for increased dexterity and fine motor control.

The array of stacked clips includes a top clip 237 which is in contact with an end of the push rod 243 opposing the thumb pushing element 250 within the chamber of the applicator, and a bottom clip 120 which at least partially protrudes from the distal end 247 of the applicator. The bottom clip 120 may be held in position via engagement of the cut-outs in the sides of the clip with the opposing protrusions 123 and 122 at the distal end 247 of the applicator. The array of stacked clips is held in a non-rotatable position via inner walls of the chamber of the applicator. For example, opposing walls 238 and 239 may abut the aligned opposing sides of each clip in the array of clips 118 so that the clips are positioned to engage protrusions 122 and 123 at the end of the applicator for opening the clips from their closed resting states to intermediate opened states for installation around everted tissue edges as described above with regard to FIG. 1.

In some examples, a substantially transparent view window 240 may be included along a portion of at least one wall of the chamber of the surgical applicator. The transparent view window 240 may comprise at least a portion of a wall of the applicator chamber perpendicular to side walls 238 and 239 of the chamber. For example, the view window may extend a distance along a wall of the chamber from the distal end 247 of the applicator, where said distance is greater than a height of the plurality of stacked surgical clips and wherein the transparent view window is perpendicular to opposing side walls 238 and 239 of the chamber. A back wall 270 opposing the transparent window 240 and also perpendicular to side walls 238 and 239 may abut aligned faces of the clips along a back side of the array of stacked clips 118. Further, an inner surface of the view window 240 may abut aligned faces of the clips along a front side of the array of stacked clips 118. The transparent view window may assist a user in operation of the applicator. For example, the view window may permit a user to determine whether or not a sufficient number of clips are loaded in the applicator, how many clips remain loaded in the chamber, and positional information of the clips in the applicator.

In this example embodiment, the push rod 243 interfaces with a top portion of top clip 237 via a clip interfacing element 245 coupled to an end of the push rod 243 opposing the thumb pusher element 250. Further, in this example, a spring element 246 is included around a portion of the push rod between the pusher element 245 and an inner wall feature 221 within the chamber of the applicator. The spring element 246 can comprise a wire spring encircling a portion of the push rod which provides a biasing force to the push rod 243 in a direction away from the distal end 247 in order to return the push rod to an initial retracted position following an application of a downward force to the push rod via the thumb pushing element. However, in other examples, e.g., as described below, such a spring element may be omitted.

When the bottom clip 120 is pushed via the push rod 243 towards the open end 247 of the applicator, the opposing protrusions 123 and 122 of the applicator housing snap into the cut-outs in the sides of the bottom clip forcing the clip to retract and be held in place at the open end of the applicator. When a subsequent force is applied to the top portion of top clip 237 in array 118, the force is transferred through the array of clips to the top portion of bottom clip 120 which causes the opposing sides of the bottom clip to bend outwardly away from each other, thereby increasing the distance between the tips of the bottom clip to place the clip in an open position. While in this intermediate open position, the bottom clip may be positioned to encompass the tissue edges and pushed forward onto the tissue edges so that the opposing protrusions of the applicator disengage the cut-outs in the sides of the bottom clip as the clip is pushed out of the end of the applicator so that the clip returns to its closed resting state with the opposing tips engaging the everted tissue edges. In some examples, a clicking mechanism may be used to deploy a surgical clip. For example, a "click" may be performed by applying an initial force to push rod 243 to load the clip into the opposing protrusions 122 and 123 extending from end 247 of applicator 116. Deployment of the loaded clip may then be performed by a second "click" wherein the handle/trigger 250 is squeezed to apply a second force to the push rod 243 to cause the clip to protrude from the end of applicator in the expanded open position around everted tissue edges until it releases or locks into place around the tissue edges.

FIGS. 4A-4F show various viewpoints and cross-sections of an example surgical clip applicator system 402 which comprises a tubular retractor 297 within which clip applicator 116 may be inserted while performing a surgical procedure on dura 104. At 226, a top view of the surgical clip applicator system is shown. At 228, a side view of the surgical clip applicator system is shown. At 232, a detailed view of an end of the tubular retractor 297 is show for the region E shown in view 228. At 230, a perspective view of the surgical clip applicator system with the applicator inserted into the tubular retractor 297 at an angle is shown. At 234, a side view of the surgical clip applicator system with the applicator inserted into the tubular retractor 297 at an angle is shown. View 236 shows a detailed view of the region G shown in view 234.

Tubular retractor 297 may comprise a cylindrical body 283 defining an inner working aperture 281 extending from a top lip 280 to an open end 298 at the surgical site. The top lip extends around a circumference of the working aperture at a top open end of the tubular retractor 297 opposing the open end 298 and a circumference of the top lip may be greater than a circumference of the cylindrical body. For example, the inner working aperture may have a diameter of approximately 25 mm and may have a height 296 of approximately 90 mm so that applicator 116 can easily fit within the tubular retractor during a surgical procedure.

The tubular retractor 297 may further include a supporting element 282 coupled to the lip 180 at an end of the tubular retractor 297 opposing end 298. For example, during a surgical procedure, the tubular retractor 297 may be positioned via supporting element 282 so that end 298 encompasses a surgical working area over the tissues to be repaired. In order to close the tissue using the clip applicator, the applicator 116 may be inserted into the tubular retractor 297 so that the distal end 247 of the applicator extends beyond end 298 of the tubular retractor 297 toward the tissue tear so that a surgical clip may be applied to everted tissue edges along the tear.

As shown in view 234 the applicator may be tilted away from a central axis of the tubular retractor 297 so that an angle 290 is formed between a central axis of the applicator and a central axis 291 of the tubular retractor 297, e.g., a 5° angle. In this way a clip may be applied using the applicator without obstructing the view of the surgeon applying the clips to the tissues.

Figure 5A:
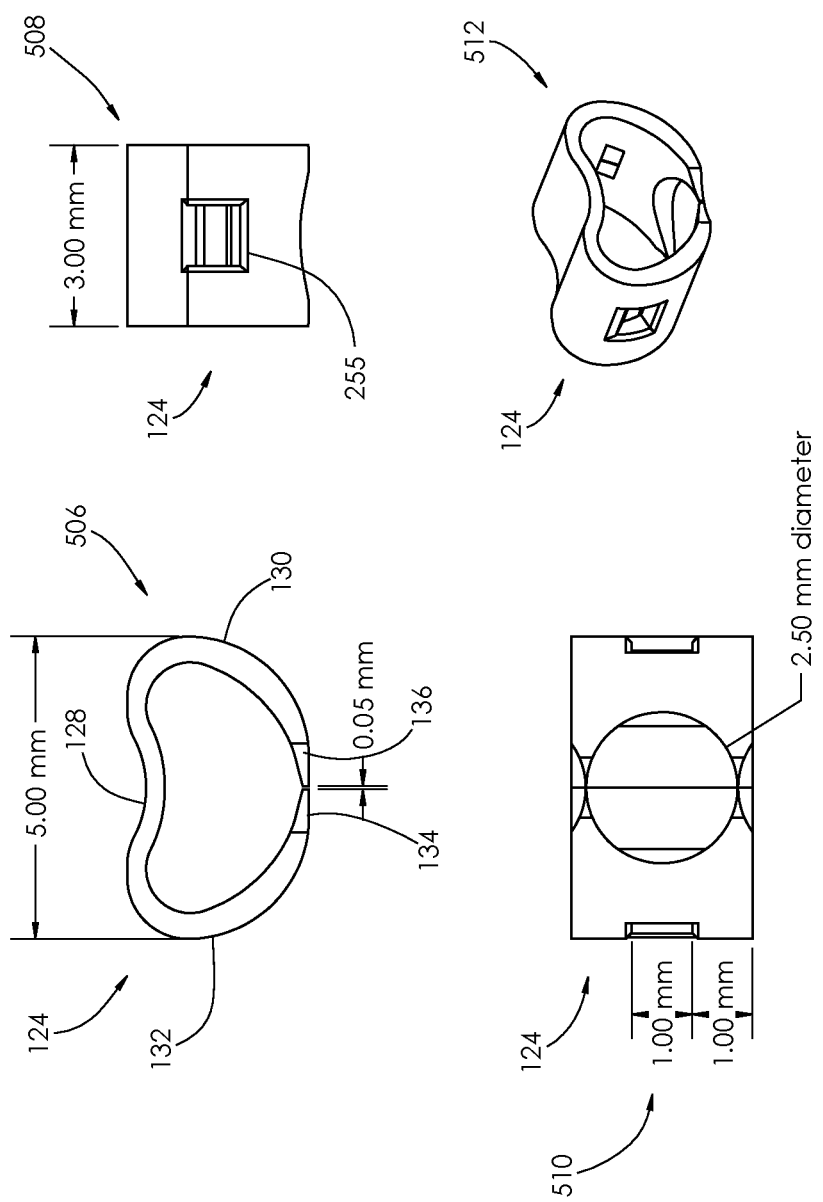
Figure 5C:
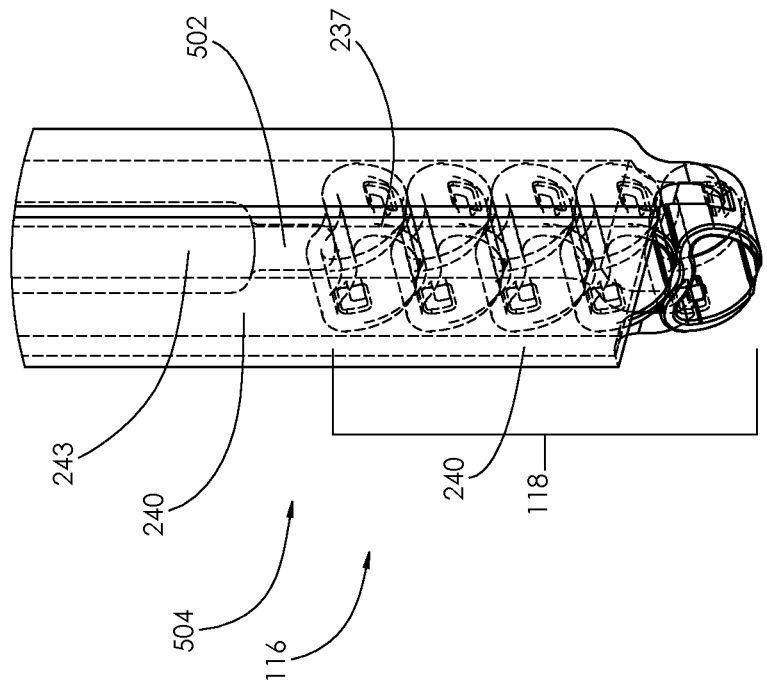
Figure 5B:
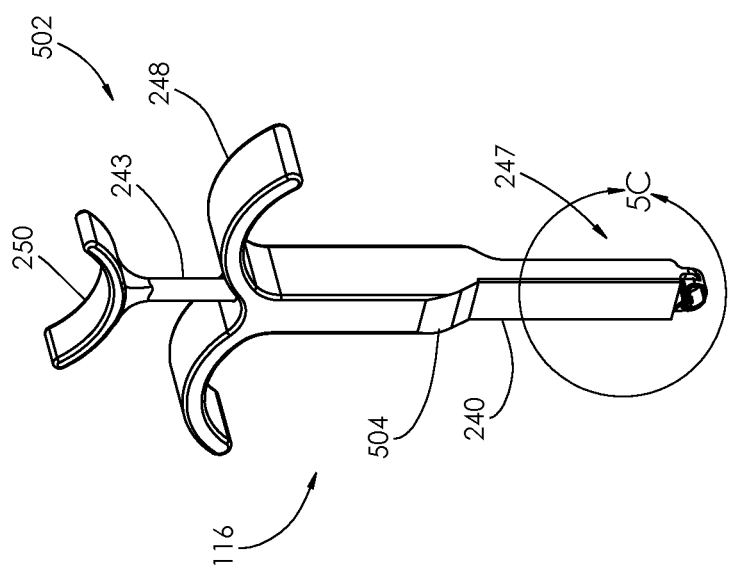
Figure 6C:
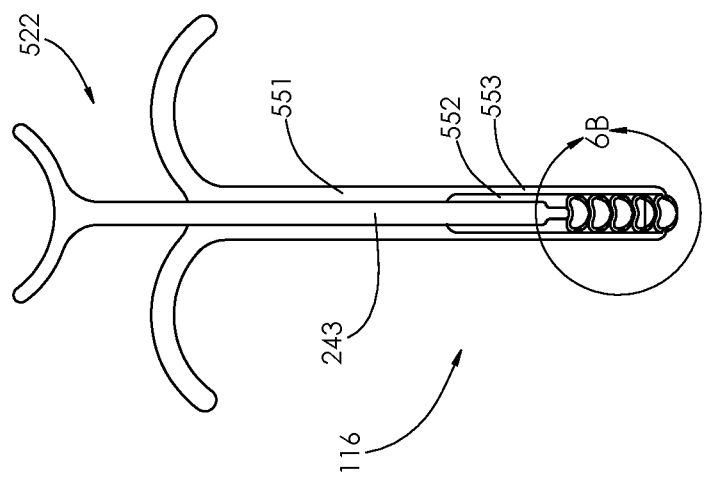
Figure 6B:
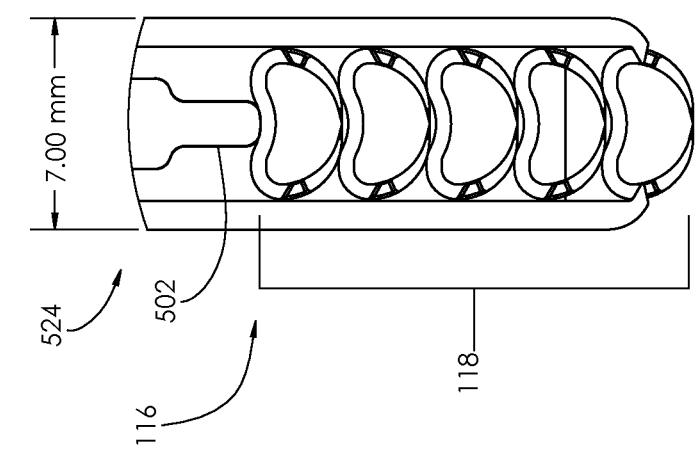
Figure 6A:
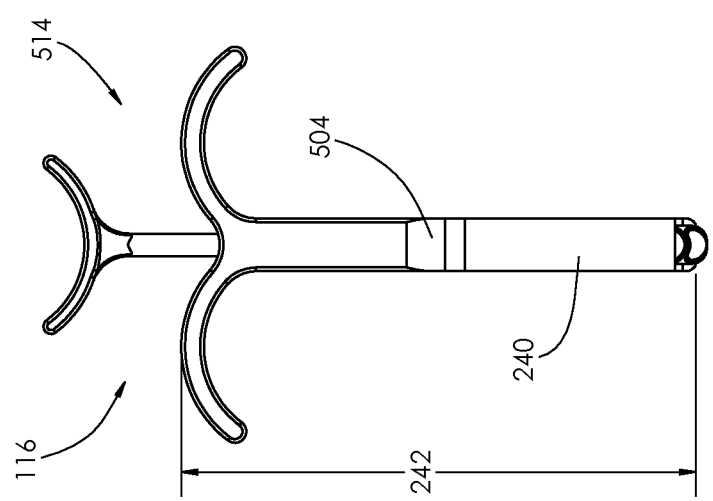
Figure 7A:
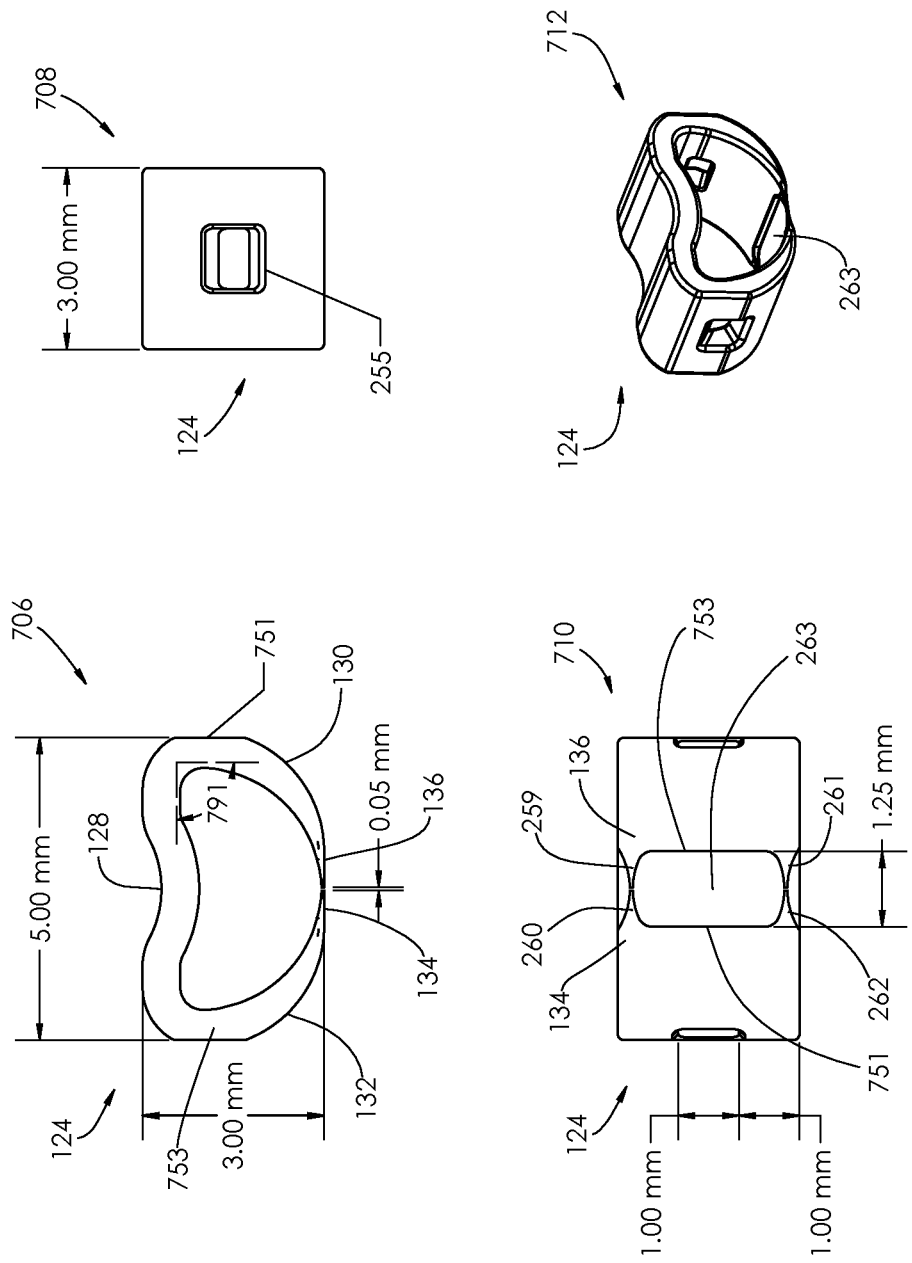
Figure 7C:
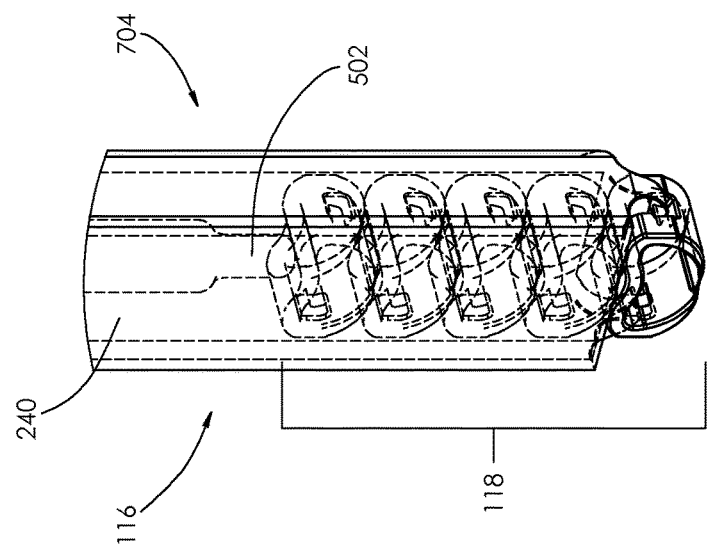
Figure 7B:
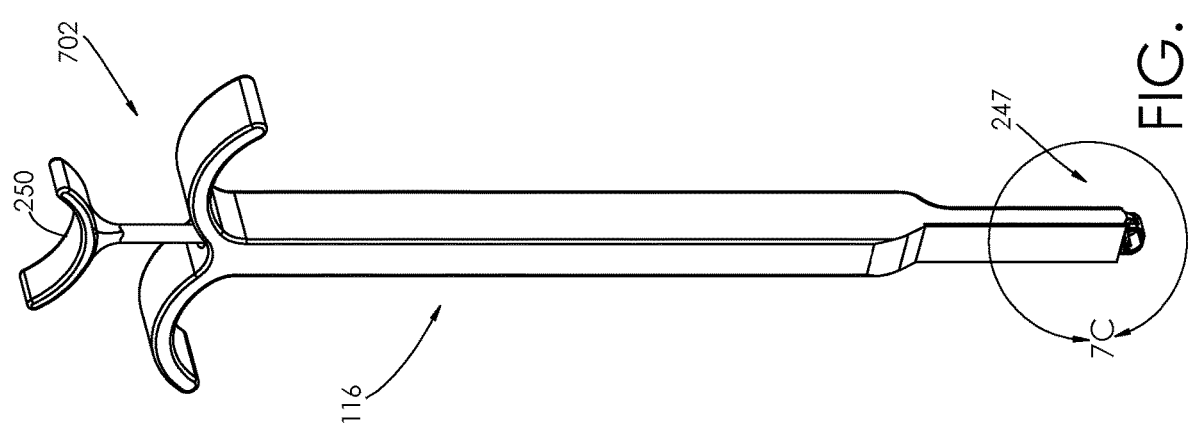
Figure 8C:
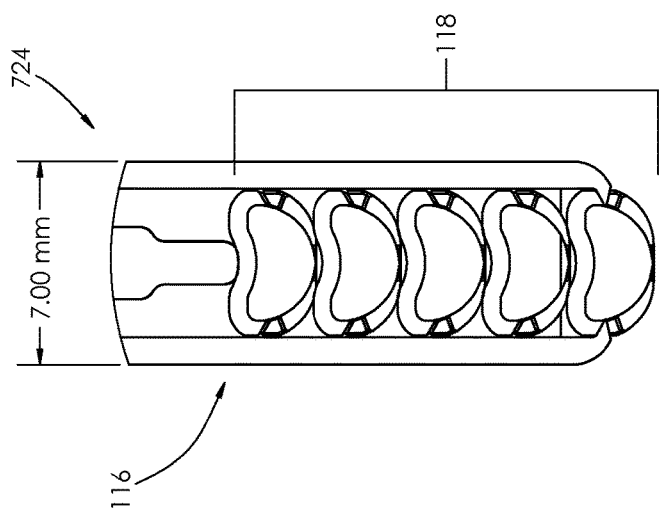
Figure 8B:
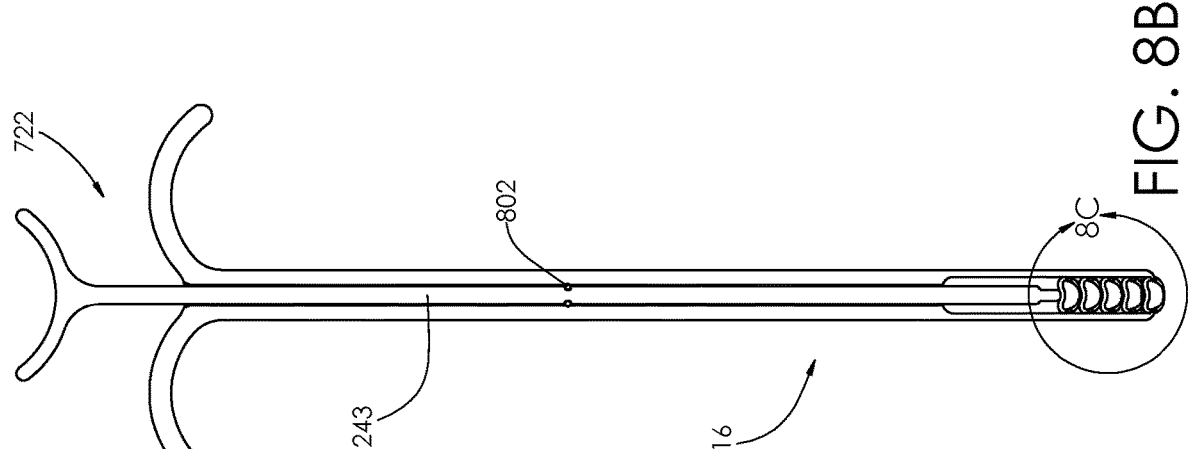
Figure 8A:
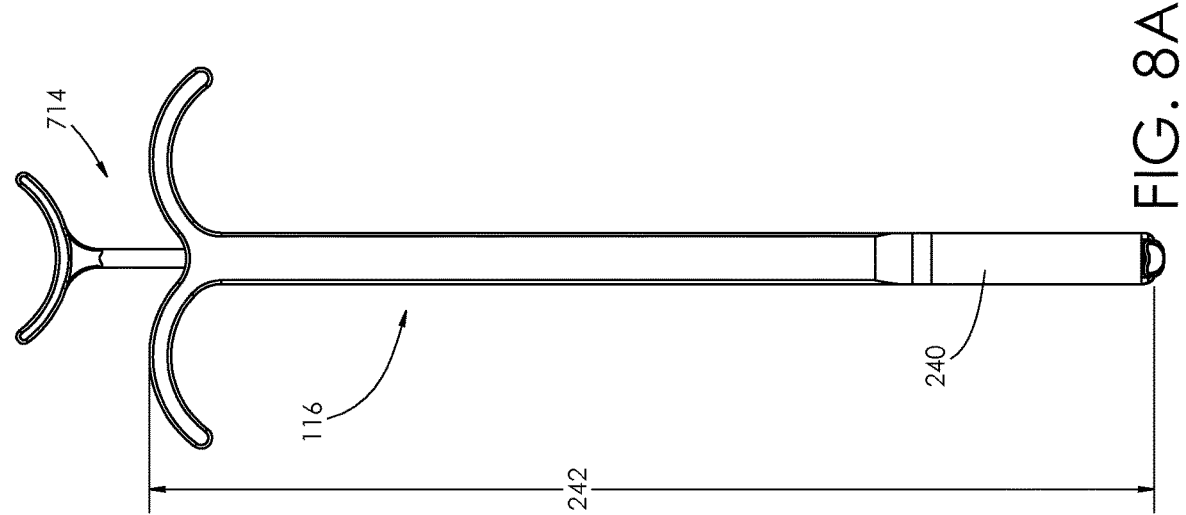
Figure 8F:
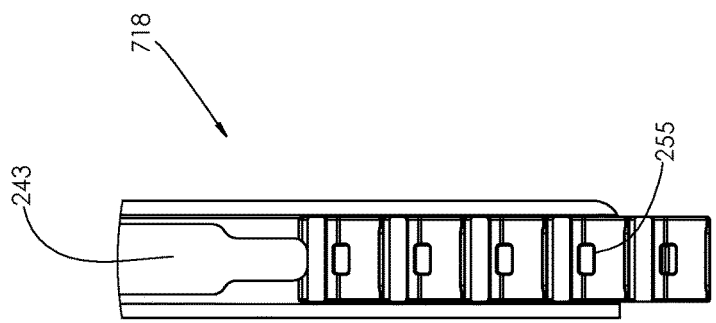
Figure 8E:
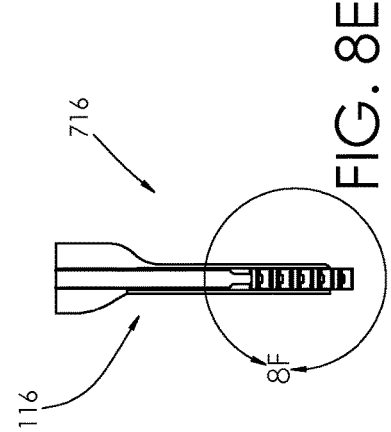
Figure 8D:
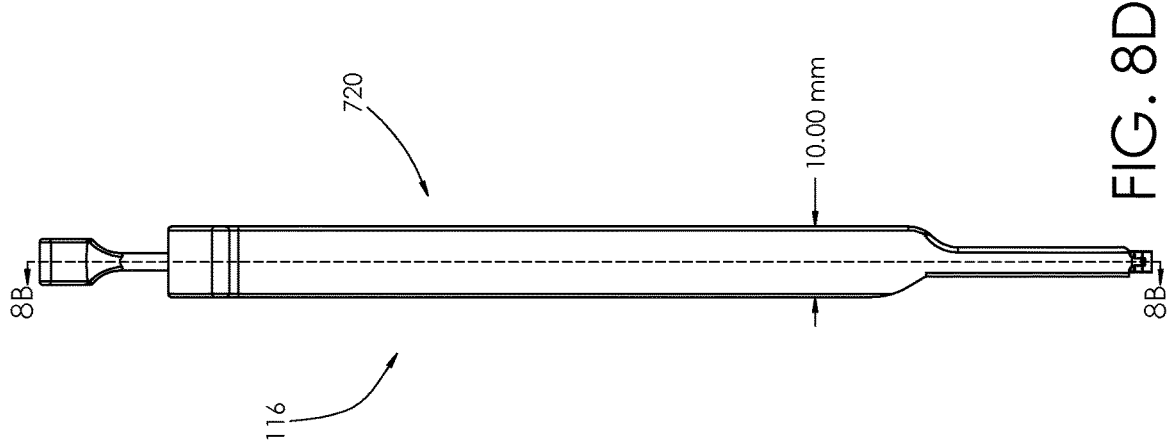

Turning to FIGS. 5A-6F, a second example embodiment of a surgical applicator 116 and surgical clip 124 is shown from various perspectives and cross-sections. At 506, 508, 510, and 512 various viewpoints of the second example embodiment of a surgical clip 124 are shown. In particular, a front face view of an example clip 124 is shown at 506, a side view of clip 124 is shown at 508, a bottom view of clip 124 is shown at 510, and a perspective view of clip 124 is shown at 512. The surgical clip shown in FIG. 5A is similar to the surgical clip shown in FIG. 2A. However, in this example, a thickness of the walls of the clip varies throughout a length of the top portion 128 of the clip. For example, as shown in view 506, a thickness of the clip wall throughout the concave top portion 128 is less than a thickness of the clip wall throughout the opposing sides 132 and 130. By making the top portion thinner, an elasticity of the clip may be increased so that a reduced amount of force is needed to cause the opposing sides of the clip to bend outwardly during installation of the clip with applicator 116.

Various views and cross-sections of the second example surgical applicator are shown at 502, 504, 514, 516, 518, 520, 522, and 524 in FIGS. 5B-6F. In particular, at 502, a perspective view of example surgical clip applicator 116 is shown. At 504, a detailed view is shown of a distal end 247 of the applicator 116 at the region A shown in view 502. The view 504 is shown at a scale of 4:1 relative to the view shown at 502. At 514 a front view of applicator 116 is shown. At 516, a detailed view is shown of cross-section B-B shown in view 514. View 518 shows a detailed view of the region C shown in view 516, where view 518 is shown at a scale of 4:1 relative to view 516. View 520 shows a side view of applicator 116. View 522 shows a cross-sectional view along cross-section D-D from view 520. View 524 shows a detailed view of region E shown in view 522 and is shown at a scale of 4:1 relative to view 522. Further, the views 506, 508, 510, and 512 of clip 124 are drawn at a scale of 8:1 relative to view 502 of applicator 116.

In this example, the push rod 243 can but need not include a spring element but instead interfaces with a top clip 237 in a stacked array of clips 118 loaded in the chamber of the applicator 116 via a pushing element 502 coupled to an end of the push rod 243 opposing the thumb pusher element. The pushing element 502 comprises an extension coupled to the push rod with a diameter and circumference less than the diameter and circumference of the push rod 243 and is held in position within the chamber of the applicator via walls 551 of the applicator. As shown in view 522, a reservoir 552 adjacent to distal end 247 is included in the chamber between the walls 551 which hold the push rod in position and the distal end 247. A thickness of walls 553 defining the reservoir 552 is less than the thickness of the walls 551 which hold the push rod 243 in position. In this example, the transparent view window 240 extends from the distal end 247 to form a wall of the reservoir 552 and terminates at a transition wall 504 wherein the width of the applicator increases in a direction from the distal end 247 towards the thicker walls 551. In this example, the height of the applicator 116 is less than the height of the applicator shown in FIGS. 2B-4F and thus may be used in open surgical applications, for example.

Turning to FIGS. 7A-8F, a third example embodiment of a surgical applicator 116 and surgical clip 124 is shown from various perspectives and cross-sections. At 706, 708, 710, and 712 various viewpoints of the third example embodiment of a surgical clip 124 are shown. In particular, a front face view of an example clip 124 is shown at 706, a side view of clip 124 is shown at 708, a bottom view of clip 124 is shown at 710, and a perspective view of clip 124 is shown at 712. In this example, each of the first and second opposing sides 132 and 130 of the clip comprises a flat portion coupled via a curved top junction to the top portion 128 and coupled via a curved bottom junction to the tip. For example, flat portion 751 is included in side 130 and flat portion 753 is included in side 132. Each flat portion may be perpendicular to the top portion 128 in the closed resting position; however, in the open position of the clip, e.g., when the opposing sides of the clip are temporarily bent outwardly during installation of the clip around everted edges of tissue, an angle 791 between the flat portion and the top portion may increase to an angle greater than 90°. Furthermore the teeth or barbs 260, 259, 262, and 261 included in the opposing tips 134 and 136 may define a rounded rectangular aperture 263 in the bottom of the clip with two opposing parallel edges 751 and 753 separated by a distance, e.g., 1.25 mm, on respective tips 134 and 136.

Various views and cross-sections of the third example surgical applicator are shown at 702, 704, 714, 716, 718, 720, 722, and 724 in FIGS. 7B-8F. In particular, at 702, a perspective view of example surgical clip applicator 116 is shown. At 704, a detailed view is shown of a distal end 247 of the applicator 116 at the region A shown in view 702. The view 704 is shown at a scale of 4:1 relative to the view shown at 702. At 714 a front view of applicator 116 is shown. At 716, a detailed view is shown of cross-section B-B shown in view 714. View 718 shows a detailed view of the region C shown in view 716, where view 718 is shown at a scale of 4:1 relative to view 716. View 720 shows a side view of applicator 116. View 722 shows a cross-sectional view along cross-section D-D from view 720. View 724 shows a detailed view of region E shown in view 722 and is shown at a scale of 4:1 relative to view 722. Further, the views 706, 708, 710, and 712 of clip 124 are drawn at a scale of 8:1 relative to view 702 of applicator 116.

The example applicator shown in FIGS. 7B-8F is similar to the applicator shown in FIGS. 5B-6F but has a height 242 greater than the height of the applicator shown in FIGS. 5B-6F. For example, the height 242 of applicator 116 shown in FIGS. 7B-8F may be approximately 138 mm so that the applicator may be used during minimally invasive surgical procedures to reach into small spaces to apply a surgical clip. Further, the flat portions of each surgical clip in the plurality of stacked surgical clips 118 in this example form interfaces along opposing sides of the array for interior walls of the clip applicator as shown in view 724.

Figure 9A:
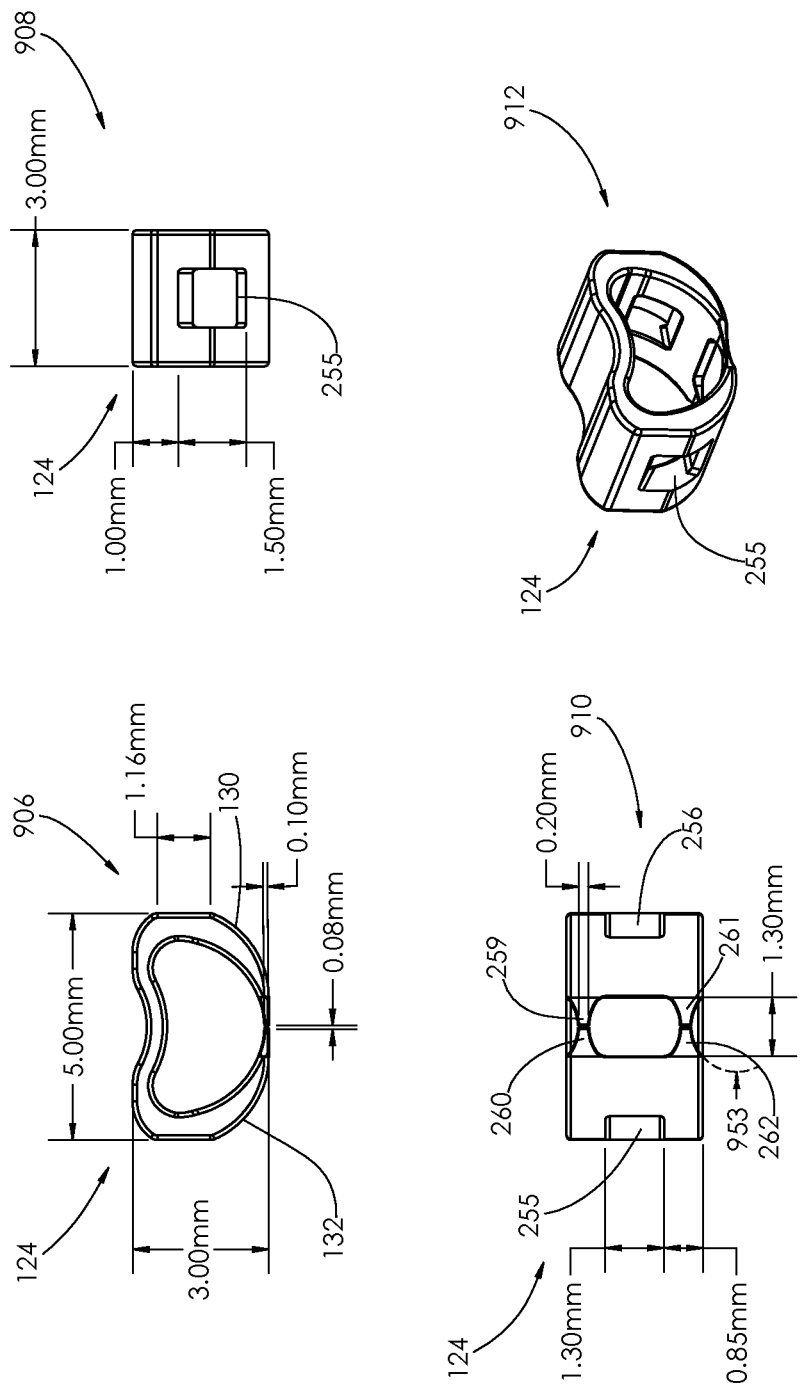

Turning to FIGS. 9A-10F, a fourth example embodiment of a surgical applicator 116 and surgical clip 124 is shown from various perspectives and cross-sections. At 906, 908, 910, and 912 various viewpoints of the fourth example embodiment of a surgical clip 124 are shown. In particular, a front face view of an example clip 124 is shown at 906, a side view of clip 124 is shown at 908, a bottom view of clip 124 is shown at 910, and a perspective view of clip 124 is shown at 912. The surgical clip shown in FIG. 9A is similar to the surgical clip shown in FIG. 7A. However, in this example, a thickness of the clip wall at the concave top portion 128 is less than a thickness of the clip wall of the opposing sides 132 and 130. This example clip also includes flat regions on each of the opposing sides to assist in alignment of an array of clips when included in a chamber of the applicator 116. Further, in this example, the teeth or barbs 260, 259, 262, and 261 included at the opposing tips of the clip do not converge to a point but instead converge to a flat edge. For example, a thickness and width of barb 260 decreases in a direction towards the opposing barb 259 to a flat edge with a length of 0.2 mm. The flat edge formed at the end of barb 260 is parallel to the flat edge formed at the end of the opposing barb 259. Further, the tapering barbs form an arc-shaped aperture adjacent to the front and back faces of the clip. For example, the decreasing outer widths of barbs 262 and 261 as they converge towards each other form an aperture defined by an arc 953 of a circle with a radius of 1 mm extending from the face of the clip into the interior of the clip at the tips.

Various views and cross-sections of the fourth example surgical applicator are shown at 902, 904, 914, 916, 918, 920, 922, and 924 in FIGS. 9B-10F. In particular, at 902, a perspective view of example surgical clip applicator 116 is shown. At 904, a detailed view is shown of a distal end 247 of the applicator 116 at the region A shown in view 902. The view 904 is shown at a scale of 4:1 relative to the view shown at 902. At 914 a front view of applicator 116 is shown. At 916, a detailed view is shown of cross-section B-B shown in view 914. View 918 shows a detailed view of the region C shown in view 916, where view 918 is shown at a scale of 4:1 relative to view 916. View 920 shows a side view of applicator 116. View 922 shows a cross-sectional view along cross-section D-D from view 920. View 924 shows a detailed view of region E shown in view 922 and is shown at a scale of 4:1 relative to view 922. Further, the views 906, 908, 910, and 912 of clip 124 are drawn at a scale of 6:1 relative to view 902 of applicator 116.

The applicator 116 shown in FIGS. 9B-10F is similar to the applicators shown in FIGS. 5B-6F and 7B-8F. However, in this example, the push rod 243 does not include an extension element but instead comprises a rod with a constant diameter and circumference throughout the length of the rod. An end of the push rod 243 opposing the thumb pushing element is in contact with a top surface of a top clip in the array of stacked clips 118. The end of the push rod in contact with the top portion of the top clip in the array 118 is shaped to conform to the concave shape of the top portion of the clip in order to simulate the clip-on-clip contact of clips in the array 118.

Figure 11A:
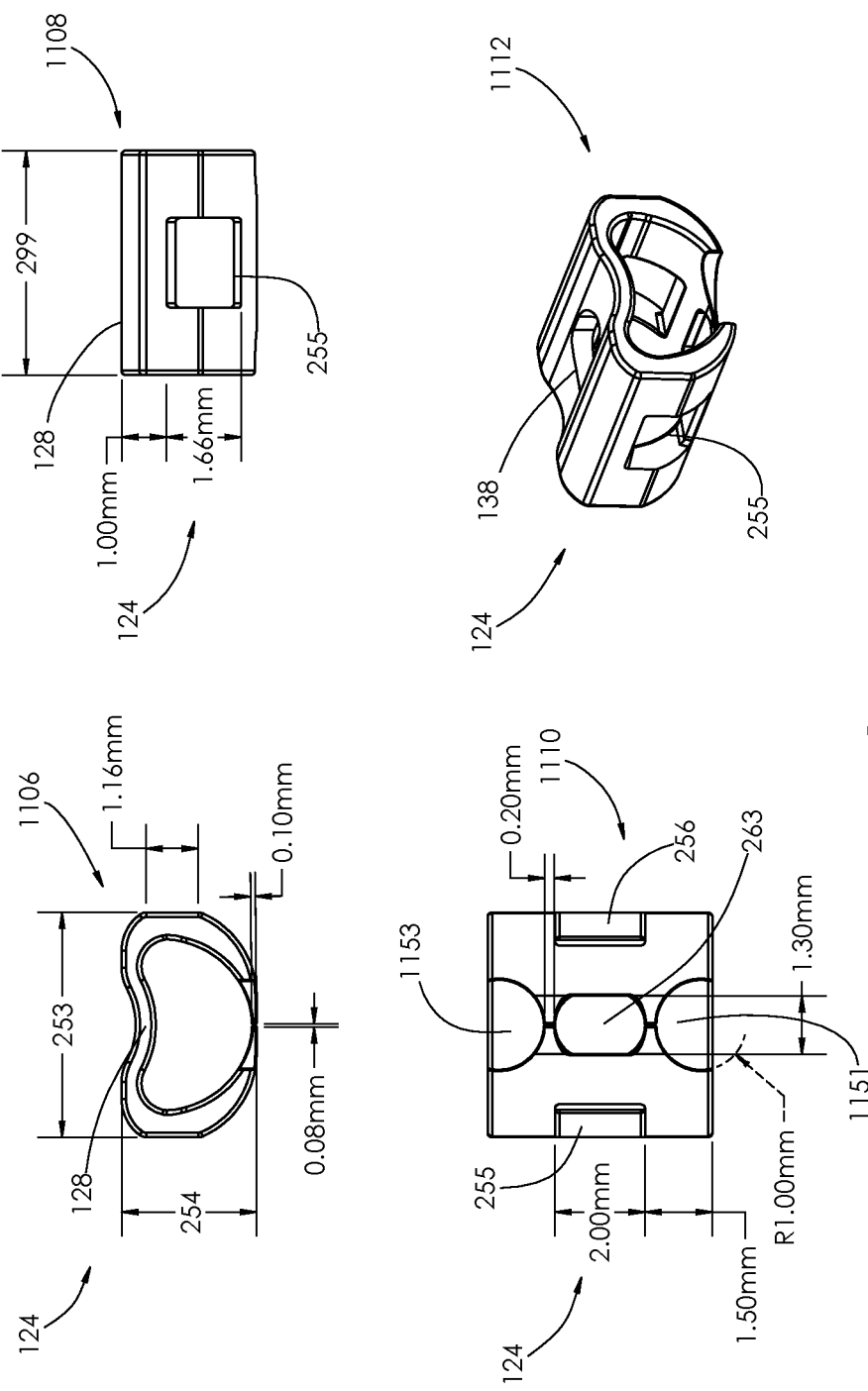
Figure 11C:
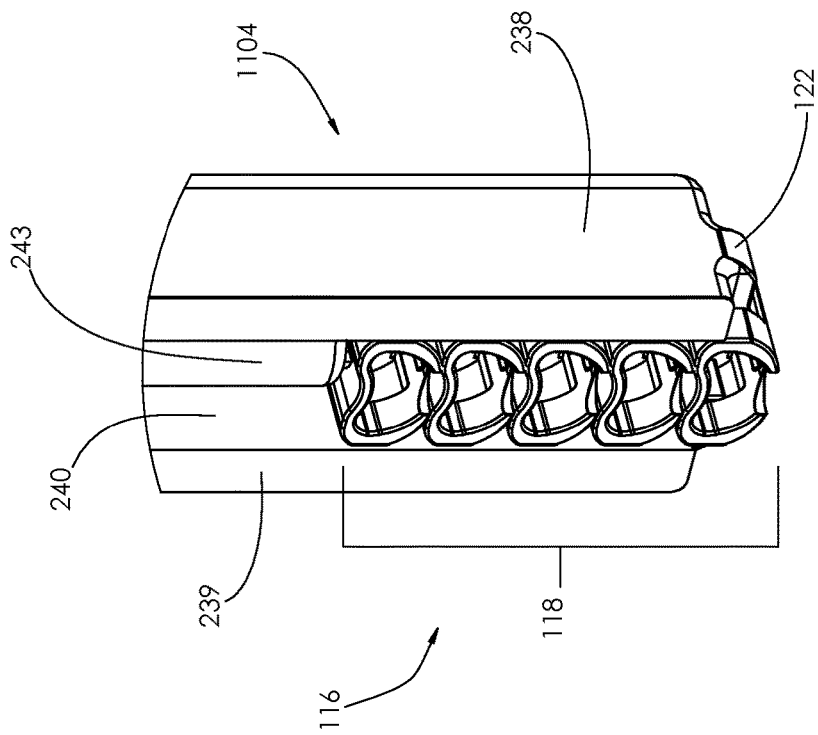
Figure 11B:
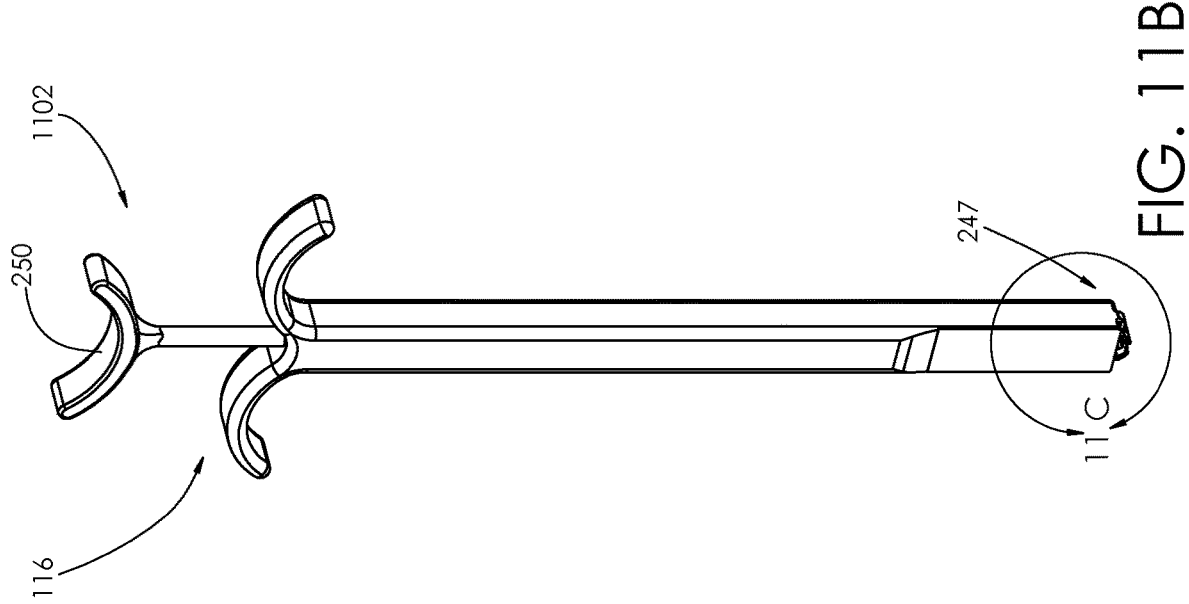
Figure 12C:
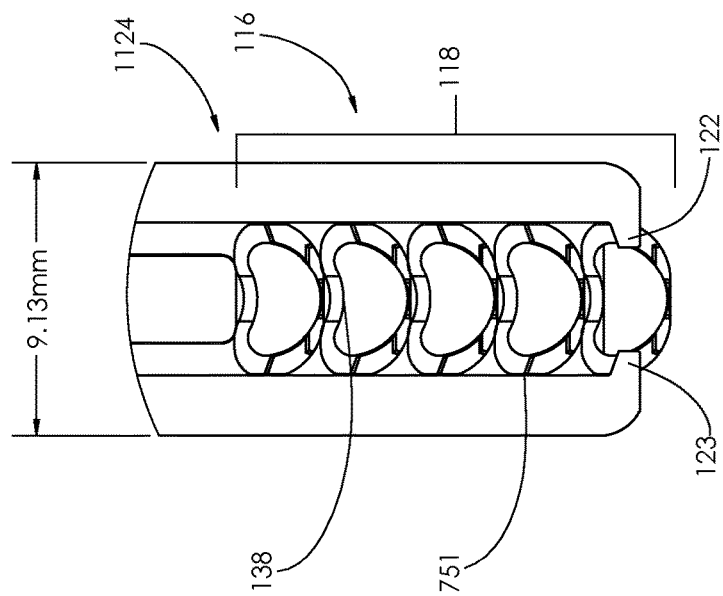
Figure 12B:
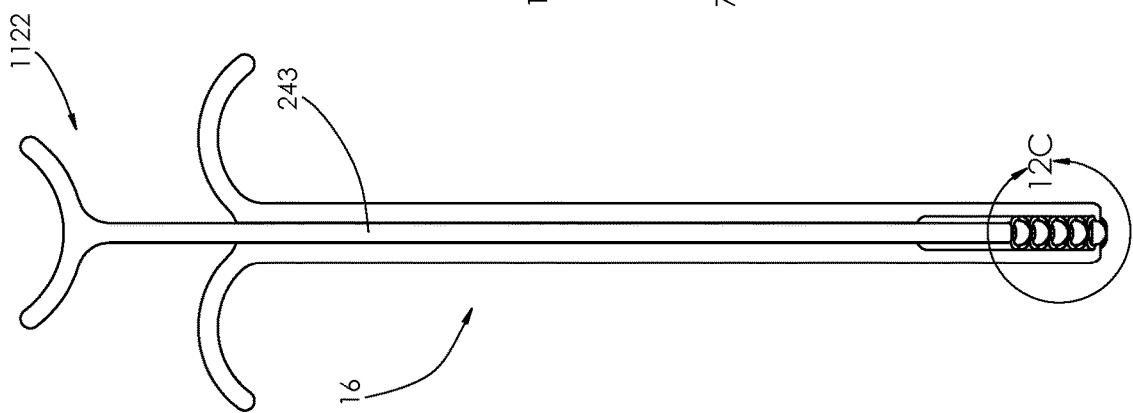
Figure 12A:
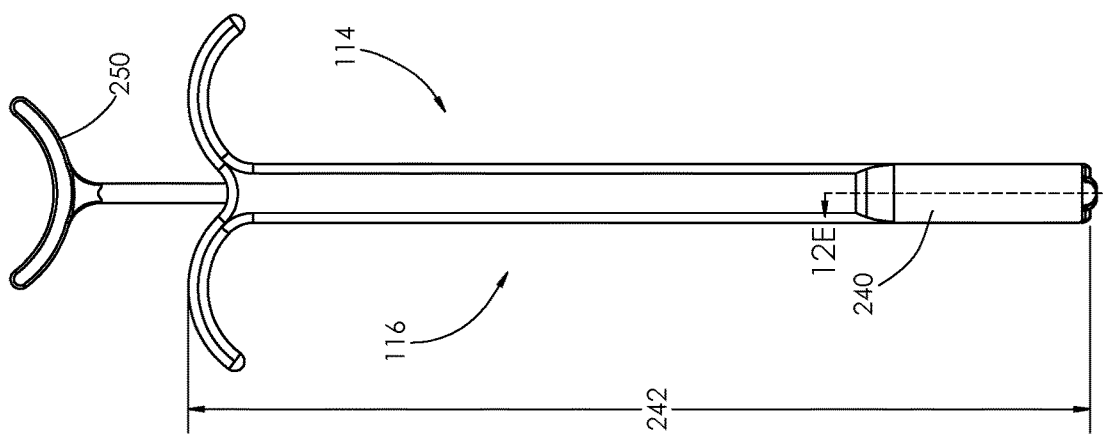
Figure 12F:
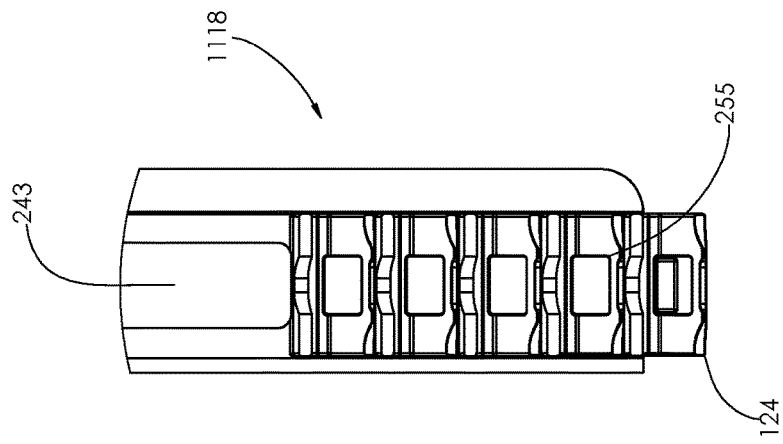
Figure 12E:
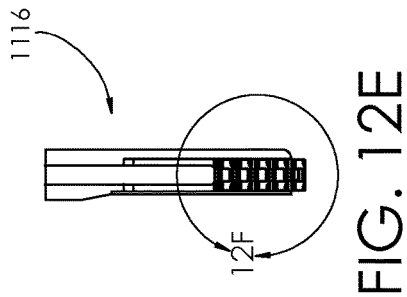
Figure 12D:
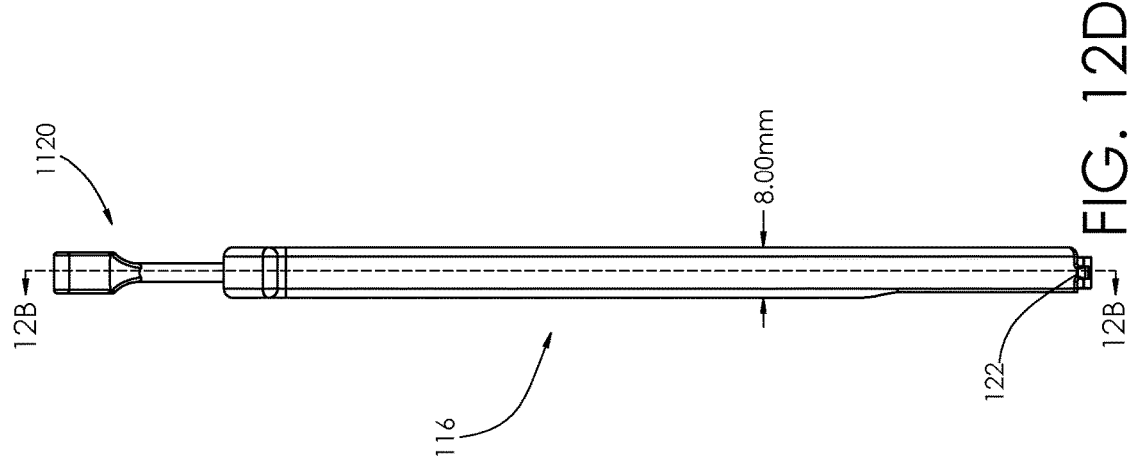

Turning to FIGS. 11A-12F, a fifth example embodiment of a surgical applicator 116 and surgical clip 124 is shown from various perspectives and cross-sections. At 1106, 1108, 1110, and 1112 various viewpoints of the second example embodiment of a surgical clip 124 are shown. In particular, a front face view of an example clip 124 is shown at 1106, a side view of clip 124 is shown at 1108, a bottom view of clip 124 is shown at 1110, and a perspective view of clip 124 is shown at 1112. The surgical clip shown in FIG. 11A is similar to the surgical clip shown in FIG. 9A. However, in this example, the length 253 and width 299 are substantially the same, e.g., both the length 253 and width 299 may be 5 mm and the top portion 128 includes an aperture 138. In this example, both the length 253 and the width 299 are greater than the height 254. Further, in this example, a size of the cut-outs 256 and 255 may be larger than previously shown, e.g., 2 mm. Further still, in this example, the barbs or teeth of the opposing tips define a central rounded rectangular aperture 263 and two opposing circular apertures 1151 and 1153 adjacent to the front and back faces of the clip and extending inwardly towards the center aperture 263. The larger cut-outs in the sides of the clips may permit wider opposing protrusions or grippers 122 and 123 on the distal end 247 of the applicator 116. These protrusions on the end of the applicator may bend inwardly from opposing sides of the applicator by a predetermined angle in order to engage the cut-outs in the clip. By enlarging the size of the cut-outs in the sides of the clips, the angles at which the opposing protrusions on the applicator bend inwardly may be decreased.

Various views and cross-sections of the fifth example surgical applicator are shown at 1102, 1104, 1114, 1116, 1118, 1120, 1122, and 1124 in FIGS. 11B-12F. In particular, at 1102, a perspective view of example surgical clip applicator 116 is shown. At 1104, a detailed view is shown of a distal end 247 of the applicator 116 at the region A shown in view 1102. The view 1104 is shown at a scale of 4:1 relative to the view shown at 1102. At 1114 a front view of applicator 116 is shown. At 1116, a detailed view is shown of cross-section B-B shown in view 1114. View 1118 shows a detailed view of the region C shown in view 1116, where view 1118 is shown at a scale of 4:1 relative to view 1116. View 1120 shows a side view of applicator 116. View 1122 shows a cross-sectional view along cross-section D-D from view 520. View 524 shows a detailed view of region E shown in view 1122 and is shown at a scale of 4:1 relative to view 1122. Further, the views 1106, 1108, 1110, and 1112 of clip 124 are drawn at a scale of 6:1 relative to view 1102 of applicator 116. As shown in view 1124, since the cut-outs in the sides of the clip in this example are larger, the opposing protrusions or grippers 123 and 122 may be made longer so that they extend a greater distance into an interior of the chamber of the applicator for greater strength and engagement with the clip loaded at the distal end of the applicator.

It will be appreciated that the configurations disclosed herein are exemplary in nature, and that these specific embodiments are not to be considered in a limiting sense, because numerous variations are possible. The subject matter of the present disclosure includes all novel and nonobvious combinations and subcombinations of the various systems and configurations, and other features, functions, and/or properties disclosed herein.

The following claims particularly point out certain combinations and subcombinations regarded as novel and nonobvious. These claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A clip applicator and at least one surgical clip, comprising:
   the clip applicator including a body and a push rod, the body having a first end and a second end, the first end having first and second inwardly turned hooks, and the push rod insertable into the second end, the push rod configured to apply pressure in the direction toward the first end;
   each surgical clip having first and second opposing sides extending from a top portion, wherein the first and second opposing sides terminate at first and second tips positioned below the top portion at a first distance between the first and second tips, thereby placing the clip in a closed resting position, the first side comprising a first cut-out and the second side comprising a second cut-out opposing the first cut-out, wherein the first cut-out is fully encompassed by the first side and wherein the second cut-out is fully encompassed by the second side, wherein the opposing cut-outs are each configured to engage the inwardly turned hooks such that while the push rod applies pressure to the top portion in a direction toward the first end, the first and second sides bend outwardly away from each other, thereby reversibly deforming the clip so as to increase the distance between the tips to a second distance, wherein the second distance is greater than the first distance, thereby placing the clip in an open position, and such that in response to said pressure applied to the top portion being removed, the clip returns to the closed resting position; and
   wherein each of the first and second tips comprises first and second points, the first point of the first tip converges to a point directly opposing the first point of the second tip, and the second point of the first tip converges to a point directly opposing the second point of the second tip.

2. The clip applicator and at least one surgical clip of claim 1, wherein the top portion is concave.

3. The clip applicator and at least one surgical clip of claim 1, wherein the top portion is flat.

4. The clip applicator and at least one surgical clip of claim 1, wherein each of the first and second opposing sides is convex.

5. The clip applicator and at least one surgical clip of claim 1, wherein the top portion includes an aperture.

6. The clip applicator and at least one surgical clip of claim 1, wherein the clip is composed of a bioabsorbable material.

7. The clip applicator and at least one surgical clip of claim 1, wherein the clip is composed of a radiolucent material.

8. The clip applicator and at least one surgical clip of claim 1, wherein a height of the clip is a dimension extending from a midpoint of the first and second tips towards the top portion, wherein a length of the clip is a dimension from the first side to the second side and wherein a width of the clip is the dimension perpendicular to the length that is not the height, wherein the height of the clip is less than the width and length of the clip.

9. The clip applicator and at least one surgical clip of claim 1, wherein each of the first and second opposing sides comprises a flat portion coupled via a curved top junction to the top portion and coupled via a curved bottom junction to the tip.

10. The clip applicator and at least one surgical clip of claim 9, wherein the flat portion is perpendicular to the top portion in the closed resting position and wherein an angle between the flat portion and the top portion is greater than 90° in the open position.

11. The clip applicator and at least one surgical clip of claim 1, further comprising:
   a surgical clip array including a plurality of the surgical clips arrayed in a stack of surgical clips;
   a chamber defined between the first end and the second end of the body of the surgical clip applicator, the chamber having an open end, the chamber housing the stack of surgical clips, said chamber being small enough to maintain the first and second opposing sides of each clip as orientated in the same direction as the first and second opposing sides of the other clips in the stack of surgical clips, yet large enough to allow movement of the individual clips in the stack of surgical clips in the direction of the tips of the clips;
   wherein the stack of surgical clips is arrayed along a central axis extending through a center of the top portion and a center midpoint between the first and second tips of each surgical clip; and
   wherein the stack of surgical clips comprises two clips in physical contact with one another.

12. The clip applicator and at least one surgical clip of claim 11, wherein the first and second opposing sides of each surgical clip in the stack of surgical clips comprises a flat portion coupled via a curved top junction to the top portion and coupled via a curved bottom junction to the tip, and wherein the flat portions of each surgical clip in the stack of surgical clips form interfaces along opposing sides of the stack of surgical clips for interior walls of the clip applicator.

13. The clip applicator and at least one surgical clip of claim 11, further comprising a top clip in the stack of surgical clips and a bottom clip in the stack of surgical clips, when said stack of surgical clips is positioned within said chamber, the top portion of the top clip is configured to interface with the push rod of the clip applicator and the first and second opposing sides of the bottom clip are configured to engage said inwardly turned hooks of the clip applicator.

14. The clip applicator and at least one surgical clip of claim 11, further comprising:
the inwardly turned hooks distal to a top clip in the array; and
the push rod configured to apply said pressure on the top clip in the array.

15. The clip applicator and at least one surgical clip of claim 11, wherein the inwardly turned hooks are coupled to the open end of the chamber.

16. The clip applicator and at least one surgical clip of claim 11, wherein the inwardly turned hooks are coupled to the body of the applicator.

17. The clip applicator and at least one surgical clip of claim 11, further comprising a transparent view window in a wall of the chamber extending a distance along said wall of the chamber from the open end of the chamber, where said distance is greater than a height of the plurality of stacked surgical clips and wherein the transparent view window is perpendicular to said opposing interior walls of the chamber.

18. The clip applicator and at least one surgical clip of claim 1, wherein a height of the clip is a dimension extending from a midpoint of the first and second tips towards the top portion, wherein a length of the clip is a dimension from the first side to the second side and wherein a width of the clip is the dimension perpendicular to the length that is not the height, wherein the width of the clip is greater than at least 25% of the length of the clip.

19. The clip applicator and at least one surgical clip of claim 1, wherein a height of the clip is a dimension extending from a midpoint of the first and second tips towards the top portion, wherein a length of the clip is a dimension from the first side to the second side and wherein a width of the clip is the dimension perpendicular to the length that is not the height, wherein the first cut-out is an aperture centered along the width of the clip between the first and second points of the first tip, and wherein the second cut-out is an aperture centered along the width of the clip between the first and second points of the second tip.

20. The clip applicator and at least one surgical clip of claim 1, wherein the first and second sides bend outwardly away from each other to reversibly deform the surgical clip from the closed resting position to the open position in response to the push rod applying pressure to the top portion.

21. A surgical clip and surgical clip applicator system, comprising:
(a) said surgical clip applicator comprising:
(i) a body having a first end and a second end;
(ii) said first end having first and second inwardly turned hooks; and
(iii) a push rod insertable into said second end, said push rod configured to apply pressure in the direction toward said first end, and said pressure being applied to a top portion of said surgical clip;
(b) said surgical clip, comprising:
(i) first and second opposing sides extending from said top portion, said first and second opposing sides terminating at first and second tips positioned below said top portion;
(ii) said first side having first hook engaging structure; and
(iii) said second side having second hook engaging structure;
(c) said surgical clip having a closed resting position in which said first and second tips have a first distance therebetween;
(d) said surgical clip having an open position in which said first and second tips have a second distance therebetween, said second distance being longer than said first distance; and
(e) wherein said inwardly turned hooks of said clip applicator respectively engage said first and second hook engaging structure, wherein while said push rod applies said pressure to said top portion, said first and second sides bend outwardly away from each other to reversibly deform said surgical clip from said closed resting position to said open position, and wherein said surgical clip returns to said closed resting position in response to said pressure being released.

22. The system of claim 21, said first hook engaging structure being a first cut-out fully encompassed by said first side, and said second hook engaging structure being a second cut-out fully encompassed by said second side.

23. The system of claim 21, said first hook engaging structure being a first tab positioned near said first side and near said top portion of said surgical clip, and said second hook engaging structure being a second tab positioned near said second side and near said top portion of said surgical clip.

24. The system of claim 21, wherein a width of said surgical clip is greater than at least 25% of a length of said surgical clip, wherein a height of said surgical clip is a dimension extending from a midpoint of said first and second tips towards said top portion, wherein said length of said surgical clip is a dimension from said first side to said second side, and wherein said width of said surgical clip is a dimension perpendicular to said length that is not said height.

25. The system of claim 21, said body of said surgical clip applicator defining a chamber between said first end and said second end, said chamber configured to house a plurality of said surgical clips arrayed in a stack of surgical clips, said chamber being small enough to maintain said first and second opposing sides of each surgical clip as orientated in the same direction as said first and second opposing sides of the other surgical clips in said stack of surgical clips, said chamber being large enough to allow movement of individual surgical clips in said stack of surgical clips in the direction of said tips of said surgical clips.

26. The system of claim 21, wherein a height of the surgical clip is a dimension extending from a midpoint of the first and second tips towards the top portion, wherein a length of the surgical clip is a dimension from the first side to the second side and wherein a width of the surgical clip is the dimension perpendicular to the length that is not the height, wherein the first hook engaging structure is an aperture centered along the width of the surgical clip between the first and second points of the first tip, and wherein the second hook engaging structure is an aperture centered along the width of the surgical clip between the first and second points of the second tip.

27. The system of claim 21, wherein the first and second sides bend outwardly away from each other to reversibly deform the surgical clip from the closed resting position to the open position in response to the push rod applying pressure to the top portion.

28. The system of claim 21, wherein the inwardly turned hooks of the clip applicator respectively directly engage the first and second hook engaging structure.

29. The system of claim 21, wherein the top portion includes an aperture.

30. A surgical clip and surgical clip applicator system, comprising:
 (a) said surgical clip applicator comprising:
  (i) a body having a first end and a second end, said body defining a chamber between said first end and said second end, said chamber configured to house a plurality of said surgical clips arrayed in a stack of surgical clips;
  (ii) said first end having first and second inwardly turned hooks; and
  (iii) a push rod insertable into said second end, said push rod configured to apply pressure in the direction toward said first end, and said pressure being applied to a top portion of said surgical clip;
 (b) said surgical clip, comprising:
  (i) first and second opposing sides extending from said top portion, said first and second opposing sides terminating at first and second tips positioned below said top portion;
  (ii) said first side having first hook engaging structure; and
  (iii) said second side having second hook engaging structure; and
  (iv) wherein said first and second hook engaging structure is selected from the group consisting of:
   a first cut-out fully encompassed by said first side, and a second cut-out fully encompassed by said second side; and
   a first tab positioned year said first side, and a second tab positioned near said second side;
 (c) said surgical clip having a closed resting position in which said first and second tips have a first distance therebetween;
 (d) said surgical clip having an open position in which said first and second tips have a second distance therebetween, said second distance being longer than said first distance; and
 (e) wherein said inwardly turned hooks of said clip applicator respectively engage said first and second hook engaging structure, wherein while said push rod applies said pressure to said top portion said first and second sides bend outwardly away from each other to reversibly deform said surgical clip from said closed resting position to said open position, and wherein said surgical clip returns to said closed resting position in response to said pressure being released.

31. A surgical clip and surgical clip applicator system, comprising:
 (a) said surgical clip applicator comprising:
  (i) a body having a first end and a second end;
  (ii) said first end having first and second inwardly turned hooks; and
  (iii) a push rod insertable into said second end, said push rod configured to apply pressure in the direction toward said first end, and said pressure being applied to a top portion of said surgical clip;
 (b) said surgical clip, comprising:
  (i) first and second opposing sides extending from said top portion, said first and second opposing sides terminating at first and second tips positioned below said top portion;
  (ii) said first side having first hook engaging structure; and
  (iii) said second side having second hook engaging structure;
 (c) said inwardly turned hooks of said clip applicator for respectively engaging said first and second hook engaging structure;
 (d) while said inwardly turned hooks engage said hook engaging structure, and in response to said push rod applying said pressure to said top portion, said first and second tips move away from each other; and
 (e) in response to said pressure from said push rod being released, said first and second tips move toward each other.

32. The system of claim 31, wherein a height of the surgical clip is a dimension extending from a midpoint of the first and second tips towards the top portion, wherein a length of the surgical clip is a dimension from the first side to the second side and wherein a width of the surgical clip is the dimension perpendicular to the length that is not the height, wherein the first hook engaging structure is an aperture centered along the width of the surgical clip between the first and second points of the first tip, and wherein the second hook engaging structure is an aperture centered along the width of the surgical clip between the first and second points of the second tip.

33. The system of claim 31, wherein the inwardly turned hooks of the clip applicator respectively directly engage the first and second hook engaging structure.

34. The system of claim 31, wherein the top portion includes an aperture.

\* \* \* \* \*